United States Patent [19]

DiRienzo

[11] Patent Number: 6,006,191

[45] Date of Patent: Dec. 21, 1999

[54] REMOTE ACCESS MEDICAL IMAGE EXCHANGE SYSTEM AND METHODS OF OPERATION THEREFOR

[76] Inventor: Andrew L. DiRienzo, 118 Weaver Rd., Elizaville, N.Y. 12523

[21] Appl. No.: 08/854,474

[22] Filed: May 12, 1997

Related U.S. Application Data

[60] Provisional application No. 60/017,316, May 13, 1996.

[51] Int. Cl.[6] .................................................. G06F 17/60
[52] U.S. Cl. .................................................. 705/2; 705/37
[58] Field of Search ...................................... 705/37, 2, 3

[56] References Cited

U.S. PATENT DOCUMENTS

| | | | |
|---|---|---|---|
| 3,573,747 | 4/1971 | Adams et al. . | |
| 4,153,931 | 5/1979 | Green et al. | 364/200 |
| 4,677,552 | 6/1987 | Sibley, Jr. | 364/408 |
| 4,903,201 | 2/1990 | Wagner | 364/200 |
| 5,038,284 | 8/1991 | Kramer | 364/408 |
| 5,063,507 | 11/1991 | Lindsey et al. | 364/408 |
| 5,168,446 | 12/1992 | Wiseman | 364/408 |
| 5,297,032 | 3/1994 | Trojan et al. | 364/408 |
| 5,321,520 | 6/1994 | Inga et al. | 358/403 |
| 5,469,353 | 11/1995 | Pinsky et al. | 364/413.01 |
| 5,513,101 | 4/1996 | Pinsky et al. | 705/2 |
| 5,655,084 | 8/1997 | Pinsky et al. | 705/2 |
| 5,664,115 | 9/1997 | Fraser | 705/37 |
| 5,715,402 | 2/1998 | Popolo | 705/37 |
| 5,715,823 | 2/1998 | Wood et al. | 705/2 |
| 5,832,221 | 11/1998 | Jones | 375/200.36 |
| 5,835,896 | 11/1998 | Fisher et al. | 705/37 |
| 5,890,138 | 3/1999 | Godin et al. | 705/37 |
| 5,905,975 | 5/1999 | Ausubel | 705/37 |
| 5,918,208 | 6/1999 | Javitt | 705/2 |
| 5,924,082 | 7/1999 | Silverman et al. | 705/37 |

OTHER PUBLICATIONS

Baxter, Kirkman G. et al. "Wide Area Networks for Teleradiology." Journal of Digital Imaging, vol. 4, No. 1, Feb., 1991, pp. 51–59.

Seshadri, Sridhar B. et al. "Design of a Medical Image Management System: a Practical Cost–effective Approach." Computer Methods and Programs in Biomedicine, vol. 25, 1987, pp. 185–192.

(List continued on next page.)

*Primary Examiner*—Allen R. MacDonald
*Assistant Examiner*—Michele Stuckey Crecca
*Attorney, Agent, or Firm*—Westerlund • Powell, P.C.; Raymond H. J. Powell, Jr.; Robert A. Westerlund

[57] ABSTRACT

A system for transmitting, storing, retransmitting and receiving a plurality of electronic medical images, which permits diagnostic readings by physicians during irregularly occurring periods of down time, where each of the electronic medical images contains an indicia, e.g., bid price, of the priority attached to it by a patient, includes first through fourth computer systems. The first computer system includes an associated scanning device for generating the electronic medical images, the second computer system includes an electronic medical image storage memory for storing the electronic medical images in a predetermined order based on the indicia in the respective electronic medical images, the third computer system includes a first display for displaying the selected one of the electronic medical images, and the fourth computer system includes a second display for monitoring all of the electronic medical images, and an input device for changing one of the indicia in a respective one of the electronic medical images thereby changing the predetermined order. The second and third computer systems are connected by both a low speed communications channel for instructing the second computer system to download the selected one of the electronic medical images to the third computer system, and a high speed communications channel for downloading the selected one of the electronic medical images from the second computer system to the third computer system. Methods of operating this system are also described.

50 Claims, 7 Drawing Sheets

OTHER PUBLICATIONS

Rosenquist, C. John, MD. "Queueing Analysis: a Useful Planning and Management Technique for Radiology." Journal of Medical Systems, vol. 11, No. 6, 1987, pp. 413–419.

Glover, John L. "Medicine in the Nineties Expectations, Priorities, and Realities." Archives of Surgery, p. 766, Jul. 1992.

Heshmat, Shahram. "A decision model for competitive bidding." Journal of Health Care Finance, v. 22, No. 4, pp. 81–87, 1996.

Rosenberg, Ronald. "A report on New England's growing companies: healing by wire." Boston Glove, s. 1, p. 52, Jul. 1994.

PATIENT BID QUEUES

| PRICE | DATE/TIME | PATIENT |
|---|---|---|
| $100 | 12/16/97 12:09 | PATIENT001 |
| $ 95 | 12/16/97 12:04 | PATIENT009 |
| $ 95 | 12/17/97 00:01 | PATIENT005 |
| $ 90 | 12/16/97 09:12 | PATIENT007 |
| . | . | . |
| . | . | . |
| $ 80 | 12/16/97 05:45 | PATIENT002 |

PHYSICIAN'S MAIL BOX

| PRICE | DATE/TIME | PATIENT |
|---|---|---|
| $390 | 12/16/97 12:09 | PATIENT011 |
| $380 | 12/16/97 12:04 | PATIENT019 |
| $380 | 12/17/97 00:01 | PATIENT015 |
| $370 | 12/16/97 09:12 | PATIENT017 |
| . | . | . |
| . | . | . |
| $310 | 12/16/97 05:45 | PATIENT012 |

ELECTRONIC MEDICAL IMAGE STORAGE

200

| PATIENT | MEDICAL IMAGE |
|---|---|
| PATIENT001 | EMI001 |
| PATEINT002 | EMI002 |
| PATIENT003 | EMI003 |
| . | . |
| . | . |

FIG. 6

REMOTE ACCESS MEDICAL IMAGE EXCHANGE SYSTEM AND METHODS OF OPERATION THEREFOR

This application claims benefit of Provisional Application No. 60/017316 filed May 13, 1996.

BACKGROUND OF THE INVENTION

1. Field of the Invention

The present invention relates generally to diagnostic health care. More specifically, the present invention relates to methods and systems for efficient delivery of diagnostic health care. According to one aspect of the present invention, systems and corresponding novel methods are provided for directing "diagnostic medical images" from patients to diagnostic physicians while producing decentralized "diagnostic medical image" distribution with control totally in the hands of the patients and the providers. According to another aspect of the present invention, systems and improved methods for controlling the dynamics of the interaction between patients and the diagnostic physicians are implemented such that a "marketplace" for patient images and provider services is created.

2. Brief Discussion of Related Art

Throughout the discussion which follows, various terms will be used to describe the patient and the several doctors trying to diagnose the patient's condition. As an aid to understanding, the following definitions shall be adhered to:

(1) Diagnosis—The art or act of idenytifying a disease from its signs or symptoms;

(2) Provider—Same as Physician;

(3) Gatekeeper Physician—The physician that is actually working with the patient, i.e., he/she is the one that orders diagnostic tests for the patient;

(4) Patient/gatekeeper—The working unit formed by the patient and his gatekeeper physician;

(5) Diagnostic Physician—The physician who "reads" the results of a diagnostic modality to obtain a diagnosis of the patient's problem. The primary examples of these would be radiologists and pathologists; and (6) Digital or Electronic Medical Image (EMI)—A digital/electronic medical image is an ordered set of numbers in a computer bulk data file. This ordered set can be reconstructed, through the use of the computer, into an object from which a primary diagnosis could be made. This set can be the representation of a picture, a graph, a diagnostic sound recording or a recording of physician comments, e.g., audio file or ASCII text, etc. For a picture, this set of numbers determines the location of pixels that, when reconstructed on a computer monitor, would form the image. These numbers also determine, for each pixel, gray scale, color, intensity, etc. Any image (e.g. CT, MRI, . . ) that is by nature in this form or can be put into this form (e.g. x-ray, pathology slide, . . .) and from which a primary diagnosis can be read by a reconstruction of these numbers (either from a high resolution computer monitor or from a film derived from these numbers, e.g., Polaroid Helios)), is a candidate for this system.

(7) Digital or Electronic Medical Form (EMF)—this is an electronic form which contains the necessary background information on the patient. The fields on this form would include name, etc, and other indicia as discussed below;

(8) Digital or Electronic Medical Record (EMR)—This is the combination of the EMI and the EMF. It should be noted that the general term "image" or "EMI" is primarily employed, since handling of image is of primary importance in both conventional methods and methods according to the present invention; and (9) Primary Diagnosis—the assessment of some aspect of a patient's medical condition based on evaluation of a diagnostic medical image.

The first action a physician generally takes upon meeting a new patient is to try and identify the patient's medical condition or problem. Until the medical problem is identified, the medical problem can not be attacked. There are many diagnostic instrumentalities, sometimes called modalities, to aid the physician in identification of the patient's medical problem. These modalities include X-Ray, EKG, EEG, MRI, CT, NM, PET, blood tests, microscope images, etc. Each of these modalities produces a characteristic "diagnostic medical image." Often, a diagnostic provider (physician) tries to analyze, or read, the diagnostic medical image as a means of helping the gatekeeper physician arrive at a diagnosis of the patient's problems. The gatekeeper then uses this to determine a course of action. It could be said that "the better the diagnosis the better the health care."

It will be appreciated that once the image is formed, the actual "reading" by the physician does not require the patient to be present. In actual practice, there are many instances where the diagnostic physician never sees the patient.

The diagnostic health care system is very large and complex, with hundreds of thousands of providers and millions of patients. It will also be readily apparent that the diagnostic health care system is a system filled with inefficiencies and inadequacies. Because of these problems, some of which will be discussed below, both patients and diagnostic physicians suffer.

Moreover, the medical profession, in many areas has not kept pace with and taken advantage of technological improvements, notwithstanding the critical need therefor. For example, storage and retrieval systems for medical image data such as X-ray films, CAT scans, angiograms, tomograms, and MRI studies are commonly antiquated and often employ methods made popular in the 1920's. Image films used by most diagnostic physicians are still displayed on an antiquated light box.

Hospitals usually maintain large "file rooms" to store the patient image data. The X-ray film image data is typically stored in a large brown envelope approximately 14 by 17 inches which is open at one end. These film envelops can become too bulky to handle and store, especially in a complex situation in which several of these folders are needed. The weight of some film image data can often reach 15 pounds or more. Moreover, it is time consuming to obtain image data from file rooms either due to administrative backlogs, lack of specialized filing personnel, and misfiling of the image data. In addition, due to the numerous responsibilities of multiple attending physicians and multiple treatment sites, image data for a significant number of patients is often misplaced, lost, or at best, difficult to find when needed.

Typically, the physician examines the patient in his/her office after the radiological studies have been made in a hospital or diagnostic facility. These films and the information contained therein are often unavailable at the time of the examination unless duplicate films are ordered. Thus, there is a need for remote access to these image data for rapid patient assessment and therapy recommendation.

U.S. Pat. No. 5,321,520, which is incorporated herein by reference for all purposes, discloses an automated high definition/resolution image storage, retrieval and transmission system for use in hospitals capable of storing, transmitting and displaying medical diagnostic quality images for use with medical X-ray films or the like. As shown in FIG. 1, the system disclosed by the '520 patent includes components for processing the image data from patient imaging to physician usage. FIG. 1 illustrates an automated high definition/resolution image storage, retrieval and transmission system 10 for use with medical X-ray film 12. System 10 includes an image scanning and digitizing means 14 to transform the visual image from the medical X-ray film 12 or other documents into digital data, an image data storage and retrieval means 16 to store and selectively transfer digital data upon request, a telecommunication means 18 to selectively receive digital data from the image data storage and retrieval means 16 for transmission to one of a plurality of remote visual display terminals each indicated as 20 upon request from the respective remote visual display terminal 20 through a corresponding communications network 21 such as a telephone line, satellite link, cable network or local area network such as Ethernet or an ISDN service for conversion to a visual image for display at the remote requesting site.

To improve automation and tracking, a machine readable indicia or label 22 containing key patient information may be used in association with the medical X-ray film 12. As shown, the machine readable indicia or label 22 is affixed to the medical X-ray film 12 prior to scanning by the image scanning and digitizing means 14 to provide file access and identification. Furthermore, digital data from alternate digitized image sources collectively indicated as 24 and file identification may be fed to the image data storage and retrieval means 16 for storage and retrieval. The major or significant processing stages with regard to the image data flow include:

(1) PATIENT RADIOGRAPHY: The patient's body is imaged and a film is exposed as in an X ray room, MRI or CAT scan lab.

(2) FILM PREPARATION: The film(s) is developed to create a visible image with optical character recognition (OCR) readable patient identification information superimposed thereon.

(3) FILM INTERPRETATION: Commonly, a radiologist drafts an opinion letter for the film(s). This document preferably includes an OCR-readable patient identification label or standard marking area.

(4) IMAGE SCANNING AND DIGITIZING SUBSYSTEM: A scanner subsystem digitizes each patient image film and/or document on a high resolution scanner. This digitized data is transmitted by a local high speed data link to a separate or remote master storage unit. Patient identification information is read from a standard format on each file by OCR techniques and efficiently stored with the digitized image data. Enhanced scanner resolution and gray scale requirements are provided. Furthermore, to reduce data rate processing, data compaction or compression is accomplished within the scanner subsystem.

It should be noted here that in order to back-up possible data link down time or scanner down time, the scanner subsystem may include a CD-ROM data storage device of some description so that image data may continue to be digitized. The CD-ROM disk may then be manually delivered to the file room unit for subsequent use. In addition, the digitized data of one or two images may be written to a compact semiconductor memory card, e.g., a "RAM Card". This form of data storage may be used to send selected images for special purposes such as when the image data is needed in another remote location for purposes of obtaining a second opinion.

At this point in the image data flow, there is a split in which the original film data is stored as a "master" in a file room and the image disk is made available for active "on-line" use in an image storage and retrieval subsystem.

(5) FILM FILING: The patient image films may be placed in the industry standard 14 by 17 inch brown paper folders and placed on conventional filing shelves. Older films can be tagged and stored off-site to reduce the excessive inventory of films found in many hospital file rooms.

(6) IMAGE STORAGE AND RETRIEVAL SUBSYSTEM: This subsystem is a remotely controllable, automatically accessible image data subsystem to store and automatically retrieve, on-demand, the compressed digital information contained on the CD-ROM disks. The image storage and retrieval subsystem may have a high-speed data link connection to the scanning and digitizing subsystem as well as a write drive recording mechanism which is dedicated to receiving the data from the scanning and digitizing subsystem. This CD write drive can operate without interrupting remote access operations.

Remote access to the image storage and retrieval subsystem may be provided by a variety of telecommunication links. By using several CD disk drives and electronic buffering, virtually simultaneous access can be granted to several or more users. However, the medical image disk will contain relatively huge quantities of data making it impractical to send over conventional data communication links without very efficient data compression technology.

(7) TELECOMMUNICATION SUBSYSTEM: Occasionally circumstances may warrant manually making an extra copy of the patient's image files to be physically delivered to an authorized requester. However, for the system to provide broad service to the health care industry it must be able to efficiently telecommunicate image files to remote locations both cost effectively and within a reasonable time interval.

(8) REMOTE DISPLAY TERMINAL: The quality of the image available to the user is limited or determined by the receiving presentation terminal or monitor. Two specific presentation terminal types can be used, a modified personal computer terminal for use in a physician's office, hospital nurses' station and the like, and a large screen presentation terminal with remote controlled interaction primarily for operating room use. Both terminals have facilities to display the available patient directory of images, and facilities to select an image, and to enhance and zoom in on selected areas of the selected image. Image enhancement has heretofore been impractical for film-based images and thus much subtle but important pathological information has been largely lost. This is especially true of X-ray data. The ability to subtly enhance contrasted tissue areas is considered to be an important feature and benefit of the system.

A high-resolution printer of 600 dots per inch (dpi) or better permits the physician to print out selected images. This is especially valuable when the physician chooses to expand and enhance selected critical image areas since a cost effective printer would otherwise not have adequate gray scale or pixel resolution to give diagnostically useful output.

Each terminal consists of a standard high performance personal computer with one or more data source interfaces such as a RAM card, a CD-ROM disk drive or a data modem, a decompression graphics interface circuit and graphics display. The large screen presentation terminal has a large screen display for easy viewing for a surgeon who may be ten or more feet distant. The large screen presentation terminal also has an optional remote control so that an attending technician or nurse can scroll images, enhance and zoom, at the surgeon's request.

One major flaw with the automated high definition/resolution image storage, retrieval and transmission system described above is that it merely assumes that a skilled diagnostic physician such as a radiologist will be available to read each X-ray film as it is taken. This may not be the case. For that reason, several hospitals may join a Radiology Health Care Network as disclosed in U.S. Pat. No. 5,469,353, which reference is also incorporated herein by reference for all purposes.

The Radiology Healthcare Network disclosed in U.S. Pat. No. 5,469,353 provides high quality, timely medical interpretations of radiological images on a national (e.g., across the U.S.) and regional basis. The images can include images created by conventional x-ray technology, computed radiography, magnetic resonance imaging (MRI), computed tomography (CT), ultrasound imaging, nuclear medicine, and mammography equipment. The network includes the acquisition of these images from health care facilities, the conversion of these images to digital format, the routing of these converted images, the interpretation of these routed images, and the routing of the interpretations back to the originating facility. The images are routed (e.g., on a variety of high-speed digital and analog telecommunication networks) to the appropriate interpretation resource by an administrative site on the Network based on one or more requirements associated with the medical image study. The interpretation can be performed on high-resolution workstations and/or on films produced by film printers. The Network includes quality control measures which assure high image and interpretation quality. The control and tracking of images by the administrative site results in the production of a complete, signed interpretive report in a timely manner. See FIG. 2.

From the discussion above, it will be recognized that the current medical image distribution technology has the following problems and limitations:

(1) Diagnostic physicians are often restricted to the local geographical vicinity of the patient/gatekeeper who requests the medical image to be made and read. This is particularly true of traditional radiology services, but is also true of existing teleradiology services. As noted in U.S. Pat. No. 5,469,353, the diagnostic physician assigned by the administrator is the one nearest to the point where the medical image was generated. It will be appreciated this is often counterproductive, since the diagnostic physician best able to perform the reading may be on the other side of the country. For example, the victim of a car crash at 6 AM in California can take advantage of a large pool of idle radiologists already at work at 9 AM along the entire east coast.

(2) Local diagnostic providers may not be adequate for the patient's medical needs either for want of competency in a particular area or due to staffing problems, i.e., a competent diagnostic physician is not available when needed. This could result in poor health care and possibly disastrous results for the patient and, legally, for the medical facility.

(3) The patient has no choice in who reads the image once it has been made. In fact, under the current system, i.e., both the traditional and teleradiology systems, there isn't even a way for the patient to know who is available to do his/her reading, or at what price. This isn't even deemed to be relevant information for the patient.

(4) The patient has no voice in determining the fee he/she will pay for the reading. Many of the new heath plans contain provisions such as "medical savings accounts" which encourage patients to spend his/her health care dollar wisely; this is impossible to do when the fee is not known in advance.

(5) The patient has no mechanism through which to barter. For example, there are medical problems that are not time critical, since most medical problems require only reasonable-time readings not real-time readings. Therefore, a patient should be able to use that fact as leverage for negotiating a lower rate for his/her reading. But under current systems there is no mechanism for doing so. Instead, the patient who can wait a day and the patient who can wait a week for their respective readings now end up paying the same fee as that paid by an emergency patient. Moreover, one of the really peculiar things about current health care delivery systems is that the fee paid for a service is often not determined by either the person receiving the care or the person providing the care. Instead, it is determined by some third party such as an insurance company, a managed care organization, or the government.

(6) The patient has little ability to interact with the diagnosing physician; the patient usually can't even find out the status of his/her medial image reading, let alone have any control over how fast his/her image is read. For some people this is more important than for others. But if it is important, this uncertainty can have a strong negative psychological effect. Since it is not unusual for a reading to take a week, it is not unusual that a patient who is prone to worry can waste many hours fixating on his/her medical problem.

(7) The diagnostic physician has almost no control over which patients come to him for readings.

(8) The diagnostic physician can do almost nothing in choosing which patients he/she wants to do readings for. He/she can only take or reject whatever patients are sent to him from a referring gatekeeper or by the central administration of some telemedicine service. The diagnostic physician is at their mercy; he/she has no access to the overall images that need to be read at any given time.

(9) The diagnostic physician has little control over scheduling; his/her routine is determined to a large degree by forces he/she has no control over, e.g., when gatekeepers choose to send him patients, scheduling for the imaging modalities, etc. This leads to 20%–30% down time, most of the down time being of short duration (approximately 15 minutes) and being unpredictable as to when it will occur. This inefficiency leads to major increases in the overall cost of diagnostic health care. Existing diagnostic health care systems, including those employing telemedicine, do not address this issue.

(10) The diagnostic physician has little ability to control his/her fees. The gifted provider could charge more if his/her services were regionally available even though the local marker for his/her particular services does not warrant an increase in his/her fees.

(11) Diagnostic physicians, on the whole, have little ability to specialize to the degree that they might like to, since their patient pool isn't large enough, in the local region, to warrant specialization. When there is a desire for increased quality, it should be encouraged at every step. Specialization generally enhances the quality of the diagnostic services provided by the profession. If the size of the patient base could be sufficiently enlarged, e.g., made national in scope, hyper-specialization would not only be possible but cost-effective.

(12) A medical facility has to be staffed based on anticipated peak work loads, which often means that the inevitable fluctuations in patient flow cause either the diagnostic staff to be over loaded or underutilized. Moreover, these fluctuations are unpredictable and often of short duration.

(13) There is no marketplace that brings together all patients and all providers.

(14) As discussed above, a Central Administration decides which diagnostic physicians should read which images. For the large teleradiology groups, where there could be hundreds or thousands of diagnostic physicians, this is untenable. It is similar to the New York Stock Exchange telling people which stocks they should buy. It also creates additional expenses, i.e., middle men.

(15) The system is not effective in alleviating the long term escalation of provider prices. Efforts by third party payers to reduce provider fees are often only temporarily successful; and

(16) Traditional radiology is changing. It has been theorized that the country will soon have only a couple of huge radiology groups. That is, a patient will have no choice but to go to one of these. It will be appreciated that this latter trend could lead to monopolistic practices.

The several different methods for the delivery of diagnostic health care previously discussed all suffer from some or all of the problems listed in items (1)–(16) immediately above.

It is desirable that a remote access medical image exchange system include the following major features:

(1) structures to store and efficiently retrieve image data and automatically identify the data by patient name, image type, date and the like;

(2) communications channels permitting diagnostic physicians to remotely access particular patient image data from the system in near real time;

(3) communications channels to quickly and affordably access image data from the gatekeeper's office;

(4) a combination of hardware and software to enhance the medical images by both contrast enhancement and zooming for improved diagnostics;

(5) software and corresponding hardware permitting the patient/gatekeeper to quickly ascertain the time by which the medical image reading will be completed and, if necessary, reschedule the reading of the medical image;

(6) software and corresponding hardware permitting the patient/gatekeeper to direct the medical image to a particular diagnostic physician of choice; and (7) software and corresponding hardware permitting the patient/gatekeeper to direct the medical image to a particular diagnostic physician or group of diagnostic physicians having a particular specialty.

In other words, it is desirable to have a remote access medical image exchange method by which the patient/gatekeeper can set a price for an individual diagnostic service, and by which the diagnostic provider can use price to decide whether to accept the offer.

What is needed is a system and operating method therefor to permit bidding for the unused time of diagnostic physicians by patients who do not need real time medical image diagnosis, and/or to permit diagnostic physicians to bid on available work, and thereby provide an electronic marketplace for diagnostic services. What is also needed is a system and corresponding operating method which permits the patient/gatekeeper to designate a particular diagnostic physician to perform a particular diagnosis. It will be appreciated that these requirements are critical to efforts to increase the quality of health care while limiting the cost of health care delivery services.

SUMMARY OF THE INVENTION

Based on the above and foregoing, it can be appreciated that there presently exists a need in the art for a remote access medical image exchange system which overcomes the above-described deficiencies. The present invention was motivated by a desire to overcome the drawbacks and shortcomings of the presently available technology, and thereby fulfill this need in the art. In order to address these issues, the present invention will be discussed with respect to modern telecommunications and computer technology. However, it must be clearly understood that telemedicine is not the essence of the present invention. In fact, although the Remote Access Medical Image eXchange (RAMIX) moves images from one place to another, even that is not the essence of this invention. The essence of the invention is the use of a decentralized, i.e., self-organizing, distribution system combined with bid queues to establish a market place which allows for continuously negotiated prices with control (over who reads the images, when they are read and what the fee will be for such a reading) being totally in the hands of the patient/gatekeeper and the diagnostic physician.

An object according to the present invention is to provide a system for connecting patients with diagnostic physicians wherein the quality of diagnostic health care is improved.

Another object according to the present invention is to provide a system for connecting patients with diagnostic physicians wherein the cost of diagnostic health care is commensurate with the urgency of need and availability of resources.

Yet another object according to the present invention is to provide a system for connecting patients with diagnostic physicians wherein the control of much of the overall process is placed squarely in the hands of the patients and the diagnostic physicians.

Still another object according to the present invention is to provide a method for connecting patients with diagnostic physicians wherein the quality of diagnostic health care is improved.

Another object according to the present invention is to provide a method for connecting patients with diagnostic physicians wherein the cost of diagnostic health care commensurate with the urgency of need and availability of resources.

A still further object according to the present invention is to provide a method for connecting patients with diagnostic physicians wherein the control of much of the overall process is placed squarely in the hands of the patients and the diagnostic physicians.

These and other objects, features and advantages according to the present invention are provided by a buffer memory for storing a plurality of digital information blocks generated by a plurality of respective first users in an order established by the first users and reflecting time of arrival, wherein each of the digital information blocks is receivable by at least one of a plurality of second users, wherein each of the digital information blocks includes an indicia of the priority one of the first users attaches to an associated one of the digital information blocks, and wherein one of the second users elects to receive one of the digital information blocks responsive to the indicia of a respective digital information block.

These and other objects, features and advantages according to the present invention are provided by a storage medium for storing computer readable instructions for permitting a computer to store a plurality of electronic medical images corresponding to respective first users, to arrange the electronic medical images in an order established by the electronic labeling of the electronic medical images, and to download one of the electronic medical images to a requesting one of a plurality of second users based on this order.

These and other objects, features and advantages according to the present invention are provided by a storage medium for storing computer readable instructions for permitting a computer to store a plurality of first electronic medical images corresponding to respective first users, to store a plurality of second electronic medical images corresponding to respective second users, to arrange the first electronic medical images in a first order established by all of the first users, to arrange the second electronic medical images in a second order established by all of the second users, to download one of the first electronic medical images to any requesting one of a plurality of third users based on the order established by the first users, and to download one of the second electronic medical images to one of the third users selected by one of the second users.

These and other objects, features and advantages according to the present invention are provided by a combination including:

- a first record medium for storing computer readable instructions for permitting a first computer to store a plurality of first electronic medical images corresponding to respective first users, to store a plurality of second electronic medical images corresponding to respective second users, to arrange the first electronic medical images in a first order established by all of the first users, to arrange the second electronic medical images in a second order established by all of the second users, to download one of the first electronic medical images to any requesting one of a plurality of third users based on the order established by the first users, and to download one of the second electronic medical images to one of the third users selected by one of the second users;
- a second record medium for storing computer readable instructions for permitting a second computer to generate the first and second electronic medical images and to upload the first and second medical images to the first computer;
- a third record medium for storing machine readable instructions for permitting a third computer to monitor a relative position of a selected one of the first and second electronic medical images and for instructing the first computer to move the selected one of the first and second electronic medical images to a new position in one of the orders established by the first and the second users; and
- a fourth record medium for storing computer readable instructions for permitting a fourth computer to download the requested one of the first and the second electronic medical images.

These and other objects, features and advantages according to the present invention are provided by a system for transmitting, storing, retransmitting and receiving a plurality of electronic medical images, each containing an indicia of the priority attached to one of the electronic medical images by a respective patient, the system comprising first through fourth computer systems. Preferably, the first computer system includes an associated scanning device for generating the electronic medical images, the second computer system includes an electronic medical image storage memory for storing the electronic medical images in a predetermined order based on the indicia in the respective electronic medical images, the third computer system includes a first display for displaying the selected one of the electronic medical images, and the fourth computer system includes a second display for monitoring all of the electronic medical images, and an input device for changing one of the indicia in a selected one of the electronic medical images.

According to one aspect of the present invention, the second computer system reorders all stored electronic medical images responsive to the change of any one of the indicia associated with the electronic medical images. According to another aspect of the present invention, the second computer system is operatively connected to the first, third and fourth computer systems by dedicated communications channels.

According to still another aspect of the invention, two communications channels connect the second and third computer systems, a low speed communications channel for instructing the second computer system to download the selected one of the electronic medical images to the third computer system, and a high speed communications channel for downloading the selected one of the electronic medical images from the second computer system to the third computer system.

These and other objects, features and advantages according to the present invention are provided by a method for operating a computer system including a buffer memory storing a plurality of electronic medical images awaiting diagnosis by a diagnostic physician, each of the electronic medical images having an associated priority indicia assigned by a respective user. Preferably, the method includes steps for:

- monitoring a rate of change of position of the patient's electronic medical image relative to the plurality of electronic medical images;
- estimating a time of reading by the diagnostic physician; and
- when the velocity is unacceptable to the patient, changing the priority indicia in the patient's electronic medical image so as to instruct the computer system to reorder the plurality of electronic medical images based on the priority indicia and thereby generate an improved time of reading of the patient's electronic medical image.

These and other objects, features and advantages according to the present invention are provided by a method for operating a computer system including a first buffer memory storing a plurality of first electronic medical images awaiting diagnosis by one of a plurality of diagnostic physicians and a second buffer memory storing a plurality of second electronic medical images awaiting diagnosis by a selected diagnostic physician, each of the electronic medical images having an associated priority indicia assigned by a respective user. Advantageously, the method includes steps for:

storing a patient's electronic medical image among a selected one of the first and second electronic medical images, monitoring a rate of change of position of the patient's electronic medical image relative to the selected one of the first and second electronic medical images to thereby determine velocity through one of the first and second buffer memories, and when the velocity is unacceptable to the patient, changing the priority indicia in the patient's electronic medical image so as to instruct the computer system to reorder the selected one of the first and second electronic medical images based on the priority indicia and thereby increase the velocity of the patient's electronic medical image through the selected one of the first and second buffer memories.

These and other objects, features and advantages according to the present invention are provided by a remote access medical image exchange system including a first facility for converting a plurality of physical medical images into corresponding digital medical images and for storing the digital medical images in a remotely accessible data storage device, to thereby provide a remotely accessible electronic digital medical image database comprised of the stored digital medical images, and a second facility remote from the first facility, but in electronic communication therewith, for providing a diagnostic service provider with access to the electronic digital medical image database, wherein the system is configured in such a manner as to enable the diagnostic service provider to select one or more of the digital medical images from the database for reading, at the discretion of the diagnostic service provider.

These and other objects, features and advantages according to the present invention are provided by a remote access medical image exchange system, including a first facility for converting a plurality of physical medical images for respective patients into corresponding digital medical images and for storing the digital medical images in a remotely accessible data storage device, to thereby provide a remotely accessible electronic digital medical image database comprised of the stored digital medical images, and a plurality of second facilities remote from the first facility, but in electronic communication therewith, for providing a pool of participating diagnostic service providers with access to the electronic digital medical image database, wherein the system is configured in such a manner as to enable any one or more of the diagnostic service providers to select one or more of the digital medical images from the database for reading, in accordance with selection criteria established by the diagnostic service providers and the patients.

According to one aspect of the present invention, the system also includes a device for facilitating interactive bidding by the patients and diagnostic service providers regarding the fees to be charged by the participating diagnostic service providers for the reading of one or more of the digital medical images from the database, whereby the system functions as an open electronic marketplace for the reading of digital medical images.

These and other objects, features and advantages according to the present invention are provided by a method for facilitating remote reading of medical images, including the steps of:

converting a plurality of physical medical images for respective patients into corresponding digital medical images;

storing the digital medical images in a remotely accessible data storage device, to thereby provide a remotely accessible electronic digital medical image database comprised of the stored digital medical images;

providing a pool of participating diagnostic service providers with access to the electronic digital medical image database; and wherein any one or more of the diagnostic service providers can select one or more of the digital medical images from the database for reading, in accordance with selection criteria established by the diagnostic service providers and the patients.

These and other objects, features and advantages according to the present invention are provided by a remote access medical image exchange system, including a first facility for converting a plurality of physical medical images into corresponding digital medical images and for storing the digital medical images in a remotely accessible data storage device, to thereby provide a remotely accessible electronic digital medical image database comprised of the stored digital medical images, and a second facility remote from the first facility, but in electronic communication therewith, for providing a diagnostic service provider with access to the electronic digital medical image database. Preferably, the system is configured in such a manner as to enable the diagnostic service provider to arbitrarily select one or more of the digital medical images from the database for reading, at the discretion of the diagnostic service provider.

These and other objects, features and advantages according to the present invention are provided by a remote access medical image exchange system, including a first facility for converting a plurality of physical medical images for respective patients into corresponding digital medical images and for storing the digital medical images in a remotely accessible data storage device, to thereby provide a remotely accessible electronic digital medical image database comprised of the stored digital medical images, and a plurality of second facilities remote from the first facility, but in electronic communication therewith, for providing a pool of participating diagnostic service providers with access to the electronic digital medical image database. According to one aspect of the present invention, the system is configured in such a manner as to enable any one or more of the diagnostic service providers to select one or more of the digital medical images from the database for reading, in accordance with selection criteria established by the diagnostic service providers and the patients.

These and other objects, features and advantages according to the present invention are provided by a method for facilitating remote reading of medical images. Advantageously, the method includes steps for:

converting a plurality of physical medical images for respective patients into corresponding digital medical images;

storing the digital medical images in a remotely accessible data storage device, to thereby provide a remotely accessible electronic digital medical image database comprised of the stored digital medical images; and providing a pool of participating diagnostic service providers with access to the electronic digital medical image database.

According to one aspect of the present invention, any one or more of the diagnostic service providers can select one or more of the digital medical images from the database for reading, in accordance with selection criteria established by the diagnostic service providers and the patients.

These and other objects, features and advantages according to the present invention are provided by a method for operating a computer system including a buffer memory storing a plurality of electronic medical images awaiting diagnosis by a diagnostic physician, each of the electronic medical images having an associated priority indicia assigned by a respective user. Preferably, the method includes steps for:

monitoring a rate of change of position of the patient's electronic medical image relative to the plurality of electronic medical images;

estimating a velocity through the buffer memory to the diagnostic physician; and when the velocity is unacceptable to the patient, changing the priority indicia in the patient's electronic medical image so as to instruct the computer system to reorder the plurality of electronic medical images based on the priority indicia and thereby increase the velocity of the patient's electronic medical image.

BRIEF DESCRIPTION OF THE DRAWINGS

The preferred embodiments are described with reference to the drawings in which like elements are denoted by like or similar numbers and in which:

FIG. 6 is a block diagram illustrating the various memory areas located within the clearing house computer illustrated in FIG. 3.

DESCRIPTION OF THE PREFERRED EMBODIMENTS

Figure 1:
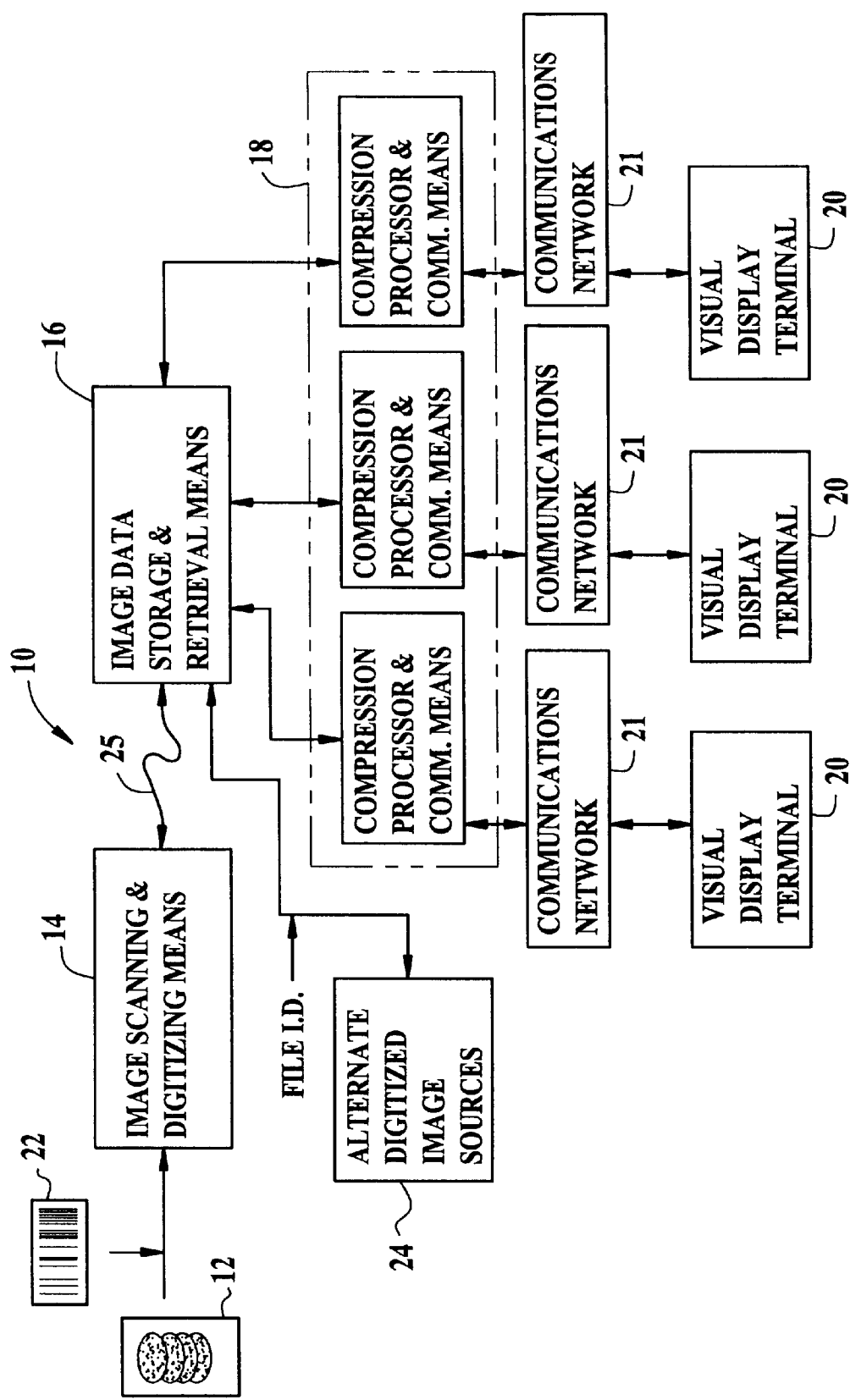
FIG. 1 is a high level block diagram of a conventional diagnostic medical image system.
Figure 2:
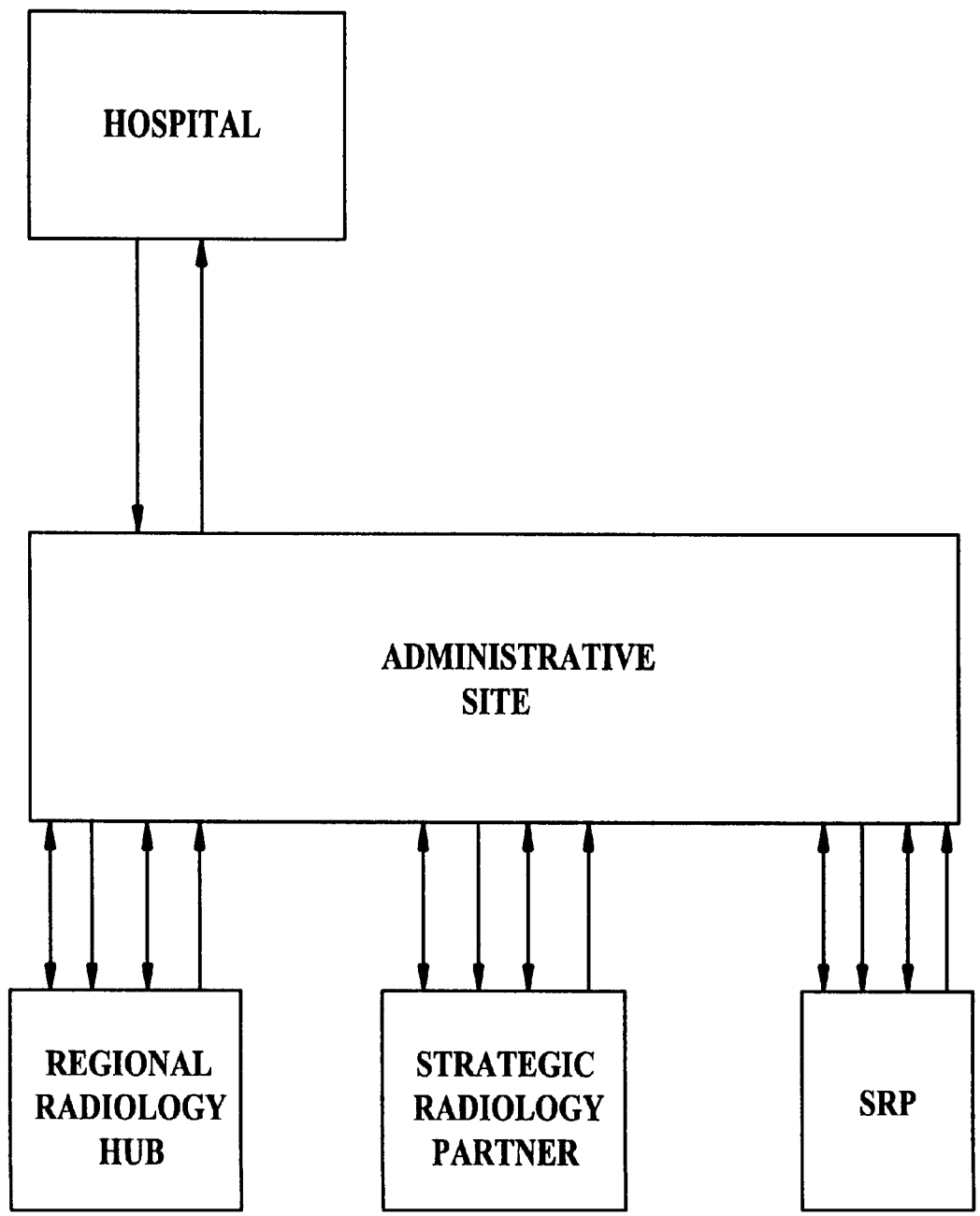
FIG. 2 is a high level representational diagram of a conventional radiology healthcare network.

As discussed in detail above, the major problems with the current diagnostic health care delivery system are that it is overpriced and inefficient. Moreover, it is run by people who don't have the patient's or the provider's best interest at heart. The overall result of the current diagnostic health care delivery system is that, at best, it does no real harm to the patient and, at worst, leaves the patient in poorer health after a course of treatment (or non-treatment) dictated by a poor diagnosis. Needless to say, the inefficiencies are financially detrimental to all concerned. The Remote Access Medical Image eXchange (RAMIX™) system and operating method therefor addresses and overcomes every one of the above-listed problems.

Additionally, the RAMIX system and corresponding operating method solve these problems by creating a new dynamic system for diagnostic health care delivery. The basic goal of diagnostic health care delivery systems is to bring the patient's image and the diagnostic provider together. In the traditional methods, this is done physically. The more recent methods, teleradiology services, for example, just use technology to bring physicians and images to one location, cyberspace. But none of the present diagnostic health care delivery systems change the way the physicians and the patients interact with one another. That is, they do not change the rules. The RAMIX system and operating method according to the present invention changes the rules.

The RAMIX system and associated operating method constitute an electronic forum which employs state of the art telecommunications equipment and a decentralized distribution clearing house to create an open marketplace for diagnostic medical services. The operating method according to the present invention may best be pictured as a cyberspace environment where patients and physicians can negotiate in a direct, often time-delayed, fashion with each other and with their respective communities as a whole. In addition, this is done continuously, i.e., on a case-by-case and provider-by-provided basis. Thus, the RAMDX system changes the rules, i.e., the dynamics, which govern the interactions between patient and provider.

Advantageously, the RAMIX operating method according to the present invention starts by having digitized patient images sent to a Clearinghouse Computer (CHC). It will be appreciated that the CHC (200) advantageously can be a mainframe computer or a dedicated server. The image is then placed in one of two separate and different markets areas, so-called Patient Bid Queues (PBQs) and Provider Mail Boxes (PMBs). Preferably, the choice between PBQ and PMB is controlled solely by the patient/gatekeeper physician. Diagnostic physicians advantageously can access both the PBQ and PMB and examine the contents of each before deciding if they want to do a reading. If they do, the diagnostic physician downloads the image(s) and begins the diagnosis. Advantageously, the patient/gatekeeper and the diagnostic physician preferably decide which diagnostic physician is going to do the reading and how much the diagnostic physician is paid for this reading. The RAMIX system acts only as a forum which allows transactions or interactions between the patient/gatekeeper and the diagnostic physician to occur.

Beneficially, the invention is based on two facts, namely, the fact that the typical diagnostic physician has one or more periods of downtime in the course of a normal day and the fact that most patients require reasonable time readings and not real time readings. More specifically, it is estimated that a diagnostic physician can be without medical images to read 25–30 percent of the time. Considering that radiologists average somewhere between $225,000 and $450,000 a year, this is extremely inefficient. Additionally, the vast majority of diagnostic images need to be read in a reasonable time, not real time.

One of the original objectives of and motivation behind the present invention was to develop a system, based on modern technology, that would take advantage of these two facts in order to provide better diagnostic health care delivery. Advantageously, the present invention evolved into a system and corresponding operating method which addresses all of the problems and inadequacies of the presently available technology described above.

Before discussing the various features and details of the RAMIX system and operating method, several aspects of the present invention will first be discussed briefly in overview in order to provide a useful framework for the subsequent detailed description. These aspects are as follows:

(1) The RAMIX system creates a marketplace which is based in cyberspace and which functions as a direct barter system between the patient and the diagnostic physician. It should be mentioned that market forces, i.e., supply and demand, are allowed to operate freely. It will be appreciated that competition flourishes in this environment; by virtue of the methodology according to the present invention, diagnostic physicians compete against each other for images to read, while patients compete against one another for a diagnostic physician's time.

(2) The RAMIX system according to the present invention is a true market; only the buyers and sellers, that is, patients and diagnostic physicians, determine who reads what image and how much is paid for that service. In fact, there is no guarantee that at any point in time there will be images to read. Moreover, there is no guarantee that images placed on the system will eventually be read. Unlike the stock market, there need be no "market maker" or other type of organizer, although this possibility is not excluded. The RAMI system functions only to establish a means for the community of providers to interact with the community of patients.

(3) The RAMIX system provides a self-organizing distribution system wherein the Patient Bid Queues and Provider Mail Boxes are designed to be totally controlled both by the patient/gatekeeper and the diagnostic provider, simultaneously. The diagnostic physician who ultimately reads a particular image is not determined by the RAMI system. The RAMIX system no more determines this than the phone company determines who you should call. Therefore the RAMIX system according to the present invention is not controlled by a bureaucrat, i.e., an administrator at the central office of a teleradiology service, or some other third party. It will be appreciated that this distribution system is specifically designed to address the problems stemming from provider inefficiency, which are due to provider downtime and lack of control thereof (4) The RAMIX system according to the present invention provides a specialized bid mechanism, which is based on ordered sets of queues for individual bid amounts. The system and corresponding operation method allow patients to barter with the entire diagnostic physician community as a whole while, at the same time, providing diagnostic physicians the means to survey the entire pool (database) of images that require reading at any given moment.

(5) The RAMIX system and corresponding methods of operation permit constant monitoring of the image's progress through either the PBQs or the PMBs by the patient/gatekeeper. Preferably, the patient/gatekeeper, when connected to the RAMIX system, can monitor how fast his/her image is moving through the queue chosen by the patient/gatekeeper. The patient/gatekeeper then has the option to change the selected queue and, therefore, the bid price the patient/gatekeeper is willing to pay for the reading. This permits the patient/gatekeeper to adjust the velocity of the medical image through the RAMI system so as to enable an earlier completion time for the reading more to the patient/gatekeepers liking. In essence, the ability to reselect the PBQ or position in the PMB where the medical image of interest resides allows for continuous negotiating of the bid price for the reading service. It should be mentioned that the reselected position could establish a lower priority, i.e., bid price, if the patient/gatekeeper determines that the medical image is moving through the selected PBQ too rapidly. For example, if the patient is scheduled for a consultation in three days, the patient/gatekeeper may select or reselect a PBQ which has an average two day velocity, i.e., a medical image placed in that particular PBQ will probably be read in 48 hours of less, so that the reading will be completed before the consultation with the gatekeeper and at the lowest possible price.

(6) Within the RAMI Clearing House Computer are located Patient Bid Queues (PBQs), which contain a pointer or link to patient electronic medical images. Each PBQ has an associated bid that all of the patients in that PBQ are willing to pay the diagnostic physician to have their medical image read. Preferably, PBQs are arranged in descending order at increments, e.g., 5%, of the average price that the patient/gatekeeper is willing to pay for the reading. In an exemplary case where the average price for a reading is $100, the PBQs would be established indicating prices of $120, $115, $110, $105, $100, $95, $90, $85, $80, etc. Within any particular PBQ, the images are arranged in "First In, First Out" (FIFO) order, i.e., time of receipt order. Note that the patient with the highest bid amount, and who is at the top of the FIFO order, is guaranteed to get his image read by the next diagnostic provider who is willing to do the reading for that amount, while the first diagnostic physician who decides to do a reading from this array, is guaranteed that the RAMIX software will download the image with the highest bid to him/her.

It should be noted that there could be an array of PBQs, for each additional criteria such as medical subspecialty and/or modality. For example, all EMR's for neurological MRI's advantageously can be put together into an array of queues as described above. In addition, there could also be another array of queues for all EMR's of CT's, and so on. Diagnostic providers are free to look into any of these arrays which they are qualified to read from. For example, PBQs may be established using both price and an additional criteria to form a matrix of PBQs. For example, different columns advantageously can be established for head, chest, and extremities with each row of a particular column being assigned a set price. It should also be mentioned that each row of the matrix need not reflect an uniform bid price; preferably, each row corresponds to a standard percentage change of the average price.

Additionally, it should be noted that an additional PBQ could be established to permit the diagnostic physician to provide charitable readings should the diagnostic physician choose to do so. Thus, an indigent PBQ could be established for this purpose. This PBQ would have $0.00 associated bid price. RAMIX software could keep track of each provider's charitable readings. This could then be used for a variety of purposes among which would be income taxes.

(7) The RAMIX system and operating method according to the present invention advantageously would include Physician Mail Boxes, which stores links, i.e., pointers, to electronic medical images (EMIs) arranged in fee amount order, i.e., the fee amount that each patient agrees to pay the particular diagnostic physician for his/her reading. It will be recognized that the very nature of the RAMIX system of the present invention includes no provisions obligating a patient to send an image to a particular provider. Moreover, under the inventive system and operating method, no diagnostic physician is guaranteed that images will be sent to him and no diagnostic physician is obligated to perform any readings even if medical images are specifically sent to him. Each PMB will contain arrays of queues just as the PBQ area does, but only the specified diagnostic provider will be able to enter it and download images.

(8) Advantageously, the RAMIX system and corresponding operating method can provide for distribution of biographic material on each diagnostic physician, both online and in hard copy form. Preferably, the patient/gatekeeper will refer to this biographic material so as to permit the patient/gatekeeper to make an informed choice if the patient prefers to select a particular diagnostic provider, e.g., a highly reputable specialist in the area of concern. As part of the RAMIX system, each radiologist would provide a biography with information such as medical school attended, publications, affiliations, residency, etc.

(9) According to one aspect of the present invention, the RAMIX system and operating method therefor permits the patient to negotiate with a pool of "just in time physicians". More specifically, if at any given moment the patient's bid is the highest in all of the PBQs, that patient is guaranteed that the next available diagnostic physician will address his/her image. That is, the patient is only negotiating with those providers who are free to do a reading at that particular moment and all diagnostic physicians in that "available" group are competing with each other to do the reading; thus the patient is virtually guaranteed that once the medial image is selected, the medical image will be read quickly. One of the particular advantages of the present invention is that there is no need for a functionary at a central administration location to decide which diagnostic physician has the time to do that particular reading; the diagnostic physicians do that themselves.

(10) According to another aspect of the present invention, the RAMIX system and corresponding operating method advantageously provides "just in time" medical images. As discussed above, 30% of any diagnostic physician's time is wasted during the day because the diagnostic physician has no images to read. This problem of 30% diagnostic physician downtime is exacerbated by the fact that the downtime comes in small units, e.g., 15 minutes of downtime. Moreover, the diagnostic physician cannot predict when the downtime will occur. The RAMIX system and operating method of the present invention were motivated by a desire to address this problem. Preferably, the RAMIX system addresses the problem by the combination of pooled patient medical images, and a decentralized distribution system. Moreover, the RAMIX system advantageously provides high bandwidth downlinks to the diagnostic physician performing the reading. It should be noted that the pooling preferably is accomplished through the PBQs and the pooling is possible because only "reasonable or just in time" readings are usually required, not "real time" readings. This results in images being presented to the diagnostic physician exactly at the time the diagnostic physician reaches an idle point in his/her day, i.e., "just in time" medical images.

At this point it should also be mentioned that a secondary advantage of the RAMI system according to the present invention is that it encourages efficiency on the part of the diagnostic physician. As a radiologist goes through his/her day, knowing that RAMIX is there will cause him to work more efficiently. Heretofore, the diagnostic physician knew that there were only so many images that he/she would be required to read during a typical day; thus, there was no reason for the diagnostic physician to be efficient. Now there is. Once the diagnostic physician is finished with a locally generated reading, the diagnostic physician can select and download a medical image from the RAMIX system.

(11) Hyper-specialization among diagnostic physicians is another aspect according to the present invention. Hyper-specialization occurs for two reasons. First, the diagnosing physician can restrict those allowed to place images in his/her mail box to the specialty that he/she wants. Second, each diagnostic physician advantageously can look over the Patient Bid Queues and pick from them medical images in his/her speciality area. Basically, this allows each diagnostic physician to increase his/her patient base. It should be mentioned that hyper-specialization also can lead to the creation of diagnostic physician "stars"; thus, a radiologist who is truly gifted at his/her work can demand a certain fee that he/she would not normally be able to get.

(12) Another advantageous result of the RAMIX system and associated method of operation is that it complements the existing practice of many diagnostic physicians. Moreover, because diagnostic physicians are under no obligation to do readings, the system does not inflict itself on an existing practice. Each individual physician, and only the physician, decides when he/she would like to perform a diagnostic reading on a medical image placed on the RAMIX system. The RAMIX system beneficially complements the diagnostic physician's existing practice and allows the diagnosing physician to work more efficiently.

In summary, the overall objects of the present invention are to (1) improve the delivery of diagnostic health care while (2) providing patients and diagnostic physicians more control over diagnostic services and the price paid therefor then they have currently. With this background in mind, the present invention will now be described with reference to FIGS. 3–7.

Figure 3:
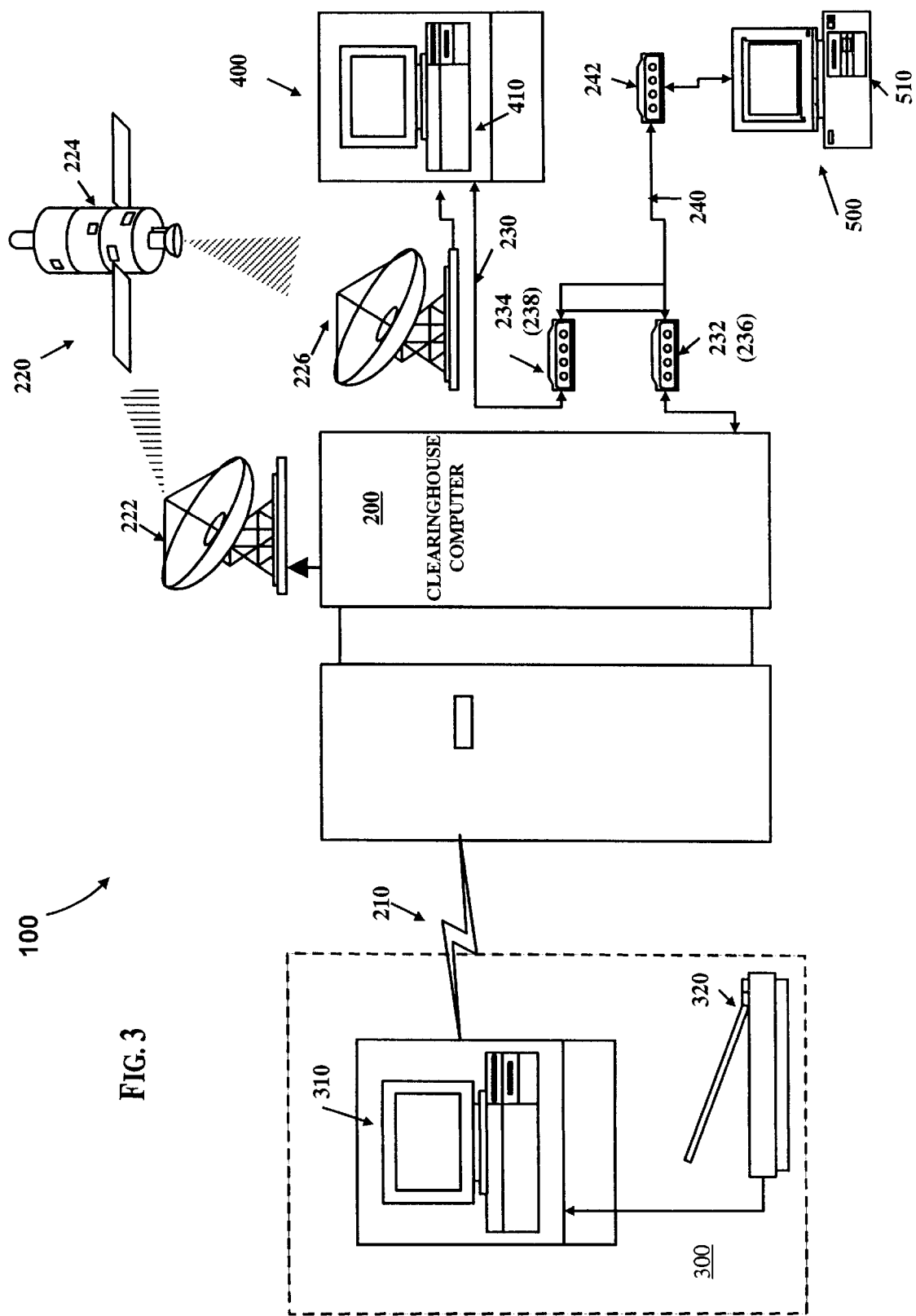
FIG. 3 is a high level representational block diagram of a system for distributing diagnostic medical images according to the present invention.
Figure 4:
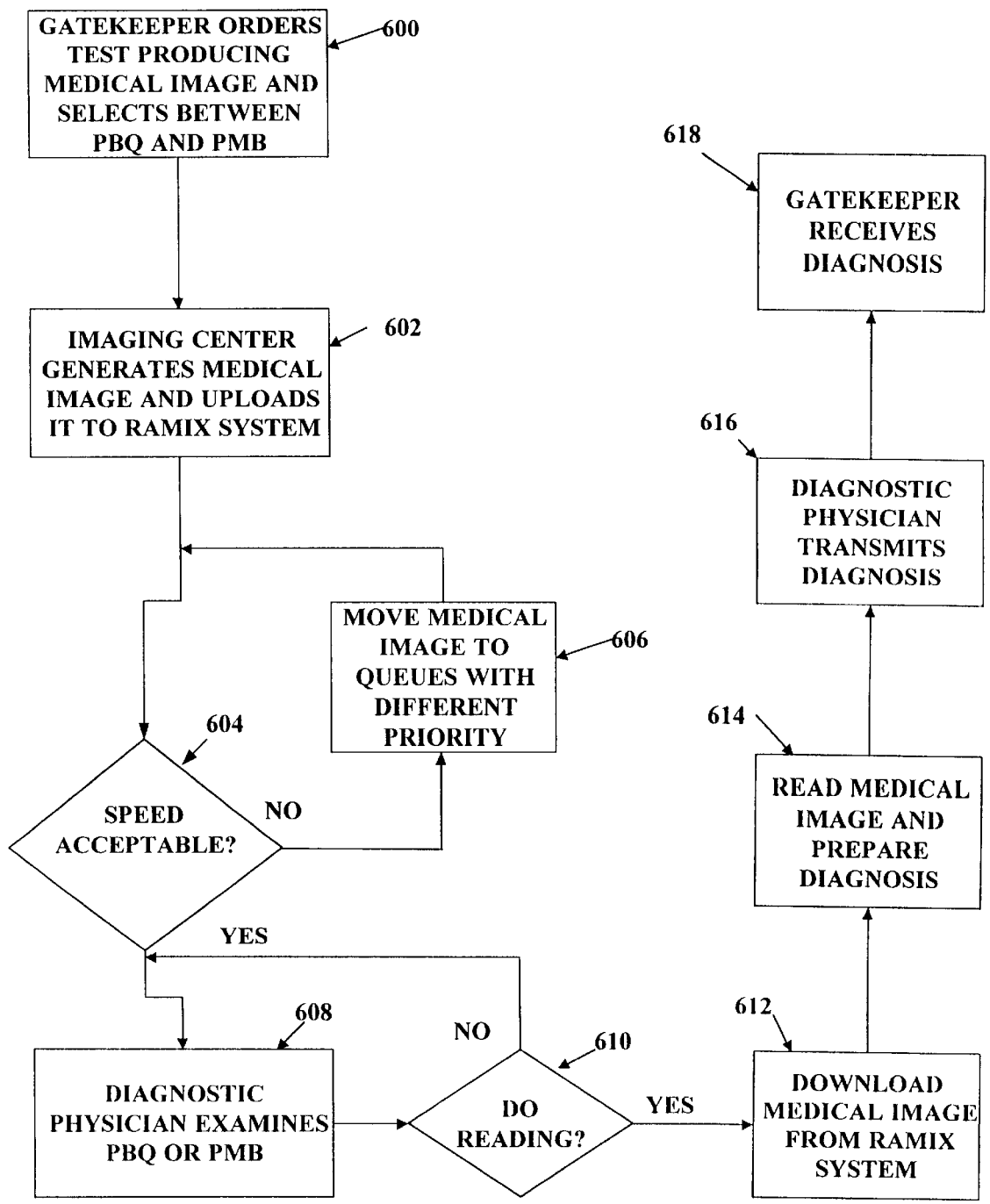
FIG. 4 is a flowchart illustrating the fundamental and supporting steps of a method of operating the system illustrated in FIG. 3.

Referring first to FIG. 3, the RAMIX system 100 according to the present invention includes a clearing house computer (CHC) 200, which advantageously receives, stores and downloads medical images requiring diagnostic readings and receives, stores and transmits reports regarding diagnostic readings performed on medical images. Preferably, the CHC 200 is a distributed computer network with redundant transmission and storage capabilities; the CHC 200 advantageously can be a server in a large scale intranet. Other hardware configurations are possible so long as the functions described below can all be performed.

Preferably, the CHC 200 is connected to a imaging center 300, which center advantageously includes, in an exemplary case, a scanner 320 which is connected to CHC 200 via a computer 310 and a communications channel 210. It should be mentioned that the scanner 320 and computer 310 depicted in FIG. 3 are exemplary only. The system disclosed in U.S. Pat. No. 5,321,520 advantageously can be used to convert conventional x-rays into EMIs on a much larger scale. It should also be mentioned that many conventional devices which produce an electronic medical image (EMI) as an output develop the medical image in digital form and then print the image as a hard copy. For example, U.S. Pat. No. 4,603,254, which patent is incorporated herein by reference for all purposes, discloses a stimulable phosphor sheet carrying a radiation image stored therein which is scanned with stimulating rays, i.e., a laser beam, to develop the stored image. The amount of light emitted from the stimulable phosphor sheet is proportional to the amount of radiation energy stored therein. The emitted light is detected and converted into an electric signal, which is subsequently converted into a digital data signal. The digital data is then used in creating a radiation image on film for use in diagnosis and subsequent storage. It should be noted that although U.S. Pat. No. 4,603,254 was discussed in U.S. Pat. No. 5,321,520, the latter patent did not appreciate that the scanner could be dispensed with when an EMI can be generated without use of an intermediate hard copy. This advantageously reduces degradation in the EMI transmitted to CHC 200. In short, while the imaging center 300 necessarily generates the EMI transferred to CHC 200, many variations of the hardware located at imaging center 300 are possible and all variations fall with the scope of the present invention.

Preferably, communications channel 210 can be a high speed dedicated transmission line, as discussed in detail below. Alternatively, communications channel 210 encompasses any method of conveying an EMI to CHC 200 in a timely fashion. The only requirement is that the digital integrity of the image be maintained. In an exemplary case, EMIs which must be read in "real time" could be electronically transferred while "reasonable time" EMIs could be transferred to a compact disc read only memory (CD-ROM) or digital Video disk (DVD) and sent by courier service to either the facility housing the CHC 200 or a facility having a dedicated high speed line to the CHC 200.

Systems according to the present invention can use various digital communication links for transferring EMIs between the imaging center 300, e.g., a hospital or a radiology clinic and the CHC 200. The digital links can include, in no particular order, (1) ATM and SONET links which operate at between 56 Mbits/sec and 2 Gbits/sec, (2) T3/DS-3 digital point-to-point services which operate at 44.746 Mbits/sec, (3) T1/DS-1 carrier point-to-point services which operate at 1.544 Mbits/sec, (4) satellite personal computer point-to-point services which operate as 400 Kbits/sec, (5) DS-0 digital services which operate at 64 Kbits/sec, (6) Frame Relay links that operate at between 9,600 bits/sec. and 1.544 Mbits/sec., (7) Ethernet or 802.3 LAN links which operate at 10 Mbits/sec, (8) IEEE 802.6 standard metropolitan area networks (MANs), and (9) ISDN (Integrated Services Digital Network) end-to-end services. The above list is not meant to be exhaustive; other forms of communications channels advantageously can be employed.

Still referring to FIG. 3, CHC 200 is also connected to the diagnostic physician's office 400 and the gatekeeper's office 500. Preferably, the diagnostic physician's office includes a high resolution graphics workstation 410 which preferably is connected to CHC 200 via both high and low capacity communications (comm) channels 220 and 230, respectively. Low speed comm channel 230 advantageously can include a pair of analog or digital modems 232, 234 connected to one another via conventional phone lines. Preferably, the comm channel 230 includes ISDN modems 236, 238, which provide additional bandwidth during the selection process, as discussed in greater detail below. Moreover, comm channel 220 advantageously includes earth stations 222 and 226, which are coupled to one another by satellite 224. In addition, the gatekeeper can include a low resolution workstation or personal computer 510, which can be connected, in an exemplary case, to CHC 200 via comm channel 240. Advantageously, comm channel 240 includes a pair of modems 232 and 242. It will be noted that modem 232 is common to both comm channels 230 and 240 since the diagnostic physician and gatekeeper will be connected to the CHC 200 at the same time only infrequently. It will also be appreciated that modem 232 advantageously can represent a modem pool handling numerous calls from various offices 400, 500.

The inventive method according to the present invention which advantageously can be used in operating the RAMIX system 100 illustrated in FIG. 3, will now be described with reference to FIGS. 4–7.

During step 600, the gatekeeper determines that a medical procedure which will ultimately result in the creation of an EMI is necessary and orders the procedure for the patient. As discussed above, the procedure is assumed to be, for the purposes of this description, a series of x-rays; in reality, the procedure is any medical procedure which can be digitized and can be provided to a diagnostic physician for reading. The gatekeeper uses his/her computer to fill out the form which instructs the imaging center 300 to perform the required procedure. It should be mentioned at this point that the form advantageously may be printed out by the gatekeeper, signed, and given to the patient. In appropriate circumstances where the gatekeeper's computer 510 is or can be interconnected to the computer 310 at imaging center 300, the gatekeeper physician can schedule the patient for the needed procedure. Preferably, the form is also sent electronically to the imaging center 300.

The computer 510 in the gatekeeper's office 500, as well as the computer 310 at the imaging center 300, include specialized software for connecting to the CHC 200. The software contains an electronic medical form (EMF), which is filled out by the patient/gatekeeper. All of the necessary medical information is entered into the EMF, with all information being entered in "fields" which can be used to track and control the reading process, as discussed in greater detail below. Preferably, the EMF can include the Acquisition Site Identification Number, Gatekeeper Identification Number and a Patient Identification Number. The operating software turns the EMF is into a computer file and electronically attaches the digitized "diagnostic medical image" to the form. The entire computer file thus becomes the patient's Electronic Medical Record (EMR). Finally, a Document Control Number (DCN) is assigned to the patient's EMR, which advantageously allows the patient/ gatekeeper, the diagnostic physician performing the reading, and the operating system of the CHC 200 to follow (track) and access the EMR as it moves through the RAMIX system. Preferably, security measures e.g., passwords, are implemented to maintain the privacy of the patient's EMR. It will also be recognized the DCN advantageously may include identifiers to indicate such things as the acquiring modality and subspecialty within the modality, to all system users.

During step 600, the patient/gatekeeper decides whether the EMI should be read by a particular diagnostic physician, in which case the form on the gatekeeper's computer 510 will contain the PMB of the selected diagnostic physician and a bid price for the reading, or be placed in the PBQs, in which case the completed form will contain only the bid price. The patient/gatekeeper makes the decision based on the information provided by the RAMI system, i.e., the CHC 200, as discussed in greater detail below.

Figure 5:
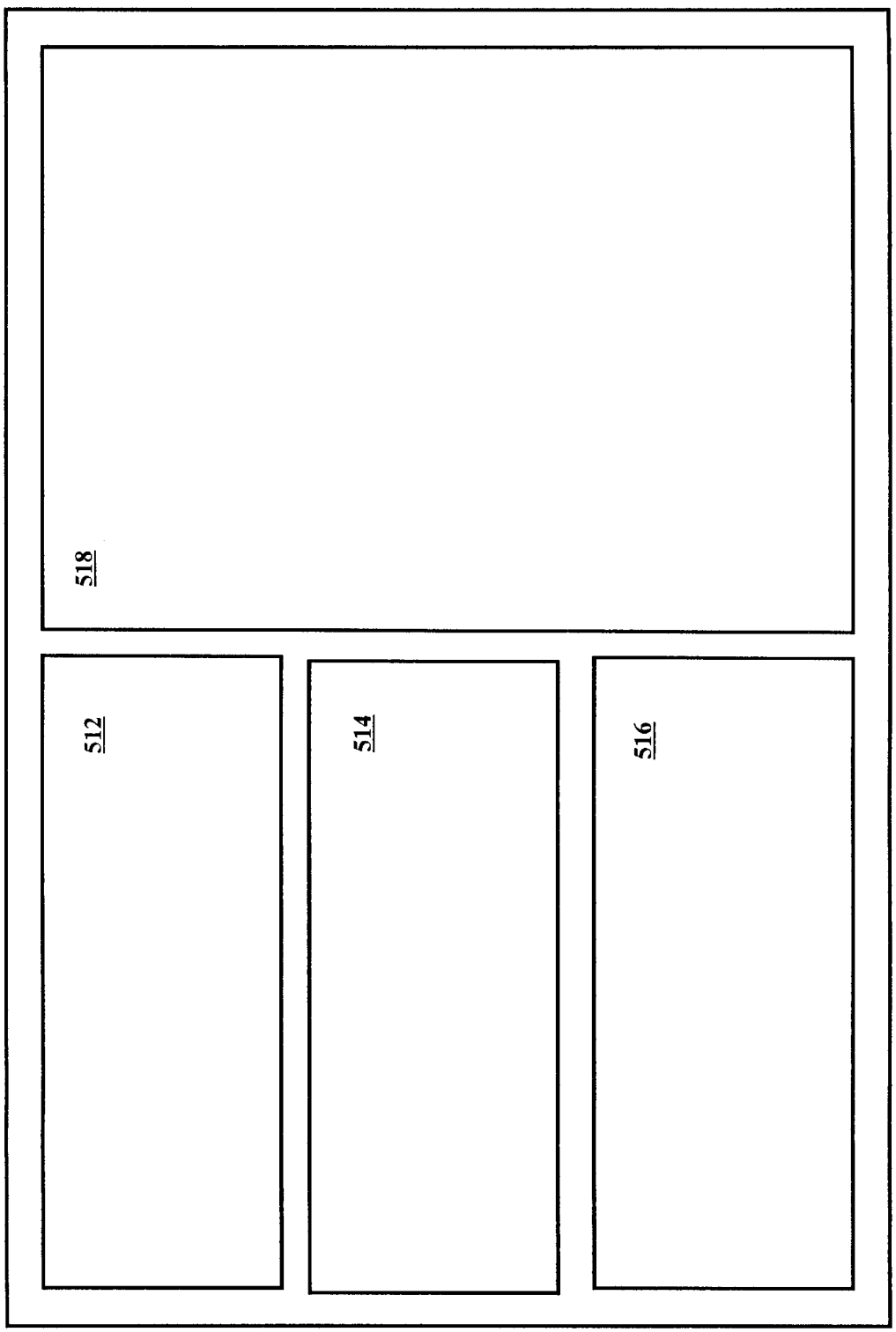
FIG. 5 is block diagram illustrating the display of a computer located at the gatekeeper's facility according to the system shown in FIG. 3.
Figure 7:
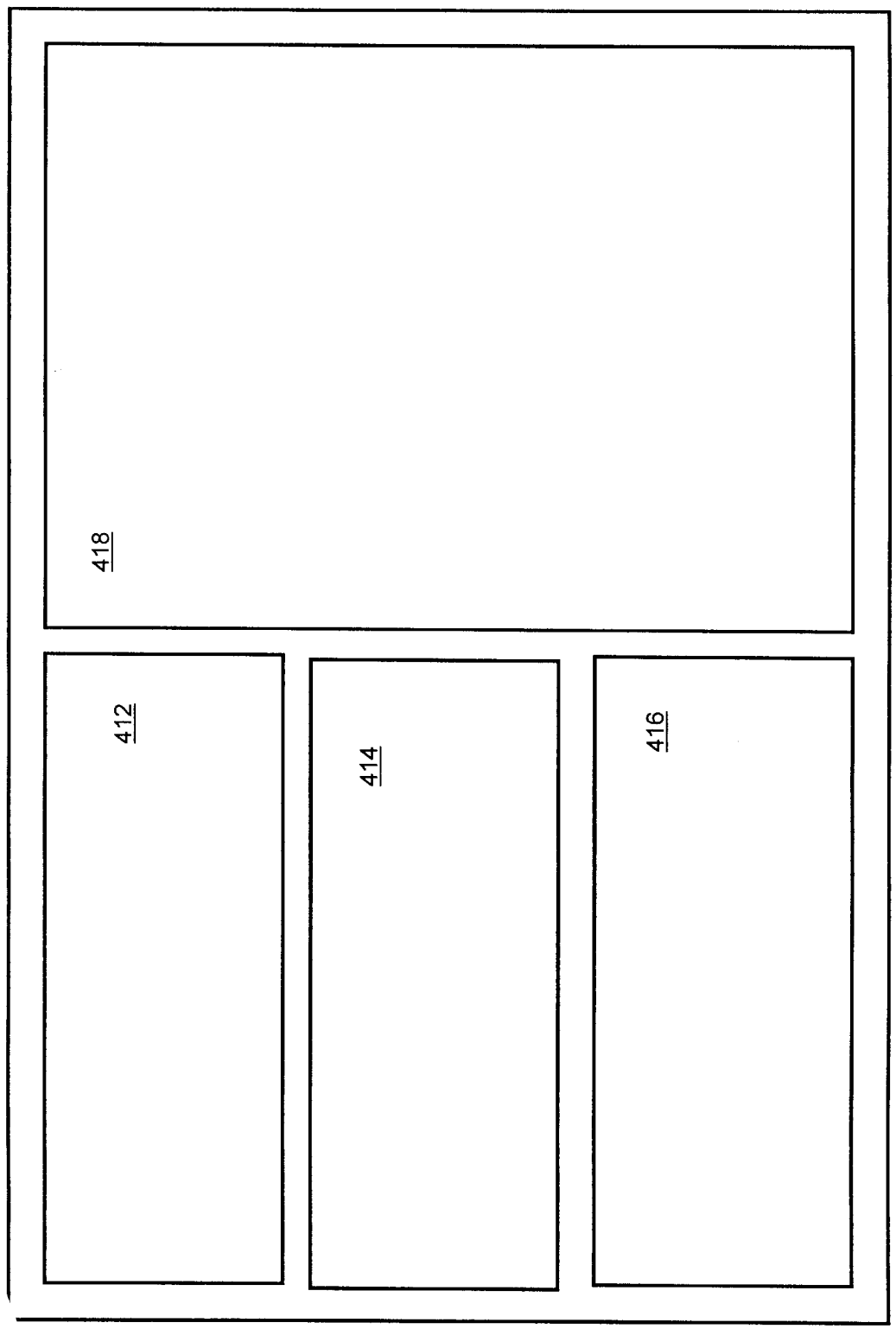
FIG. 7 is a block diagram depicting the computer screen of a computer located at the diagnostic physician's facility according to the system illustrated in FIG. 3.

As shown in FIG. 5, the display of computer 510 includes four distinct areas 512, 514, 516 and 518. Preferably, area 512 is reserved for patient data such as the form ordering the needed procedure while area 514 displays information regarding the PBQs and PMBs. In addition, area 516 is dedicated to messages such as the diagnosis performed by the diagnostic physician, which will be discussed in greater detail below. Area 516 on the screen of computer 510 advantageously may also be used to display biographical information on diagnostic physicians to the patient/ gatekeeper. Beneficially, screen area 518 allows the patient/ gate-keeper to view a low resolution version of the medical image, or a high resolution of the pertinent parts of the EMR, once the diagnostic physician's reading has been performed. It should also be mentioned that the relative sizes of areas 512, 514, 516 and 518 are for illustrative purposes only. Moreover, while the areas, which are generated by graphical user interface (GUI) software, could be resized for various tasks or according to physician preferences, preferably the areas have a predetermined size and arrangement so that the gatekeeper can readily grasp the displayed information.

In the preferred embodiment, in order for a diagnostic image to be read on the RAMIX system, the patient's EMR must be placed in either a PBQ or a PMB, as discussed above. A "field" is provided on the patient's electronic medical form to permit selection between the PBQs and a PMB. In either case, the patient's electronic medical form must also specify the bid price, i.e., the price he/she is willing to pay, for the diagnostic reading. Advantageously, a bid price need not be specified in alternative embodiments of the present invention. Alternatively, the patient advantageously can "shop around" for a diagnostic physician based on a specified asking price posted within the biographical information resident in the RAMIX system.

It must be mentioned that only the patient/gatekeeper determines the path the EMR will take to arrive at the desk of a diagnostic physician; the RAMIX system plays no part in making this decision. Thus, the EMR could be routed to the diagnostic physician either via a PBQ or via a PMB.

It will be appreciated that in order for the patient/gatekeeper to make an educated determination of the routing to the diagnostic physician which best suits the patient's needs, the patient/gatekeeper should have access to information such as:

(1) The bid price of each PBQ and ask price for each reading physician, i.e., the nominal asking price set by each diagnostic physician for his/her respective PMB;

(2) The total number of patients in each PBQ and each PMB;

(3) The average velocity, i.e., propagation time or speed, through each PBQ and PMB;

(4) The average velocity through each PBQ and/or PMB at a given time of the day;

(5) An estimate by the RAMIX system as to approximately when a reading would normally occur based on where the patient might place his/her medical image; and (6) Detailed Biographies of all reading providers. This information is provided to the patient/gatekeeper via the computer 510 from CHC 200, preferably in area 514 of the computer's screen. It should be mentioned that once the image has been sent to the RAMIX system, the patient/gatekeeper may order his/her image moved to a different queue. In order to facilitate this decision, the patient/gatekeeper advantageously has access to the information noted above, as well as the current position in the queue of the patient's image, and the information regarding movement through the selected queue, as discussed in greater detail below.

Advantageously, the patient/gatekeeper makes use of all of the above-mentioned information available to him in deciding which is the best choice, PBQs or PMBs, for bidding on the reading of his/her medical image. Preferably, one or more of the following variables can be taken into consideration when the selection is made:

(1) The urgency of the reading;

(2) The difficulty of the reading;

(3) The expertise of the reading physician; and (4) The financial situation of the patient.

With this information in hand, the patient/gatekeeper can intelligently control the reading, in that the patient can now pick the best PBQ or PMB for his/her needs and reflective of his/her financial status.

As discussed briefly above, there are two types of locations where a patient/gatekeeper can place a medical image for reading: Patient Bid Queues (PBQs); and Provider Mail Boxes (PMBs). Together these locations create a forum or marketplace for electronic medical images and provider services, allowing patients to bid for provider services while allowing diagnostic physicians to compete with one another to provide the diagnostic services desired by the patients. With the preferred embodiment of the system and method of the present invention, negotiating is performed anonymously, not one-on-one between a single patient and a particular provider, although this possibility is not excluded. In other words, according to the system and corresponding method of the present invention, any negotiating is done en masse, not face-to-face between a particular patient and a particular provider. Which PBQ or PMB a medical image is placed in is strictly up to the patient and his/her gatekeeper physician; the RAMIX system is no more involved in this selection than the phone company is involved in selecting the telephone calls the patient makes. Of course, it will be appreciated that the RAMIX system does not permit connections to diagnostic physicians who are not subscribers.

As previously mentioned, Provider Mail Boxes (PMBs) allow patients to bid against one another for a particular diagnostic physician's time. Each reading physician is assigned his/her own Mail Box, which will contain, at any one time, a listing of all of the patients who are specifically requesting that the diagnostic physician diagnose their medical image. Within the RAMIX system, the PBM is divided into different subdirectories based on the amounts that the patients are willing to pay for the reading of their respective medical images. The patient image is listed under the amount that they are willing to pay on a FIFO basis. An exemplary arrangement of subdirectories labeled with bid prices is show in Table 1. It should be noted that a similar array could appear for each modality.

TABLE 1

| $400 | $390 | $380 | $370 | $310 | $280 |
|------|------|------|------|------|------|
| —    | —    | —    | —    | —    | —    |
|      |      | —    | —    |      |      |

The CHC 200 advantageously can provide the patient/gatekeeper with statistical information about the provider's mail box including average speed through an array of queues, the number of patients at each bid amount, and the average amount accepted by the provider to do the reading, etc. Preferably, the CHC 200 can provide additional specific information including the current status of the reading physician, e.g., whether the diagnostic physician is in town, and the asking price of the diagnostic physician for any reading. It will be appreciated from the discussion immediately above that a patient need not offer the diagnostic physician his/her asking price. The patient may decide to offer the diagnostic physician a premium, which will likely result in a short delay, or may choose to offer a discounted price, knowing that the discounted price will likely result in a longer delay.

It will be appreciated that the contents of Table 1 are changing continuously as images come in from patients and are downloaded by the diagnostic providers. In particular, the highest bid price will be changing also. This results in a situation where the bid price offered to the diagnostic physician is being continuously negotiated on a case-by-case and provider-by-provider basis. The same will hold true for the PBQs, as discussed in detail below. Advantageously, when the information is changing rapidly, the provider selects an image, as discussed with respect of FIG. 4, by choosing the next available image, irrespective of the fee offered, or choosing the next available image at the current maximum bid price. It will be appreciated that the latter choice may mean that the provider may not obtain an EMR for reading during the present downtime period.

When the patient/gatekeeper requests that a particular diagnostic provider perform the reading, the patient's EMI advantageously contains both the PMB address and an amount the patient is willing to pay for the diagnostic service. Advantageously, the patient/gatekeeper can also specify such things as the time limit for doing the reading and an alternative diagnostic physician so that, in the event that the primary diagnostic physician cannot or will not complete the patient's reading before the time expires, the patient's EMR is transferred to the PMB of a secondary diagnostic physician. As will be discussed in greater detail below, once the medical image has been sent to the CHC 200, the software operating the CHC 200 will enter the EMR into the physician's mail box and reprioritize all EMRs according to the bid amounts offered for the services. Once the physician logs on to the RAMIX system, he/she can enter his/her personal PMB using a security code, and look over the directory of EMR labels identifying medical images that are waiting to be read. The diagnostic physician will determine whether to read or reject any particular image. Moreover, the diagnostic physician alone decides what fees he/she will accept or reject for his/her reading. It will be appreciated that for those physicians who are truly gifted in the profession the demand for their diagnostic services will be high and, thus, they can justifiably charge higher amounts for their services, according to the basic law of supply and demand in a free and open marketplace. It should also be mentioned that the RAMIX system places no restrictions on how fast the medical images must be read, unlike those in the patient bid queues.

It should also be recognized that the above configuration of the PMB is an exemplary arrangement; other arrangements are possible. For example, all medical images sent to a particular physician's mail box advantageously may be shown in a consolidated listing sorted on the bid price offered for the reading and the date-time the EMR containing the EMI is received by the CHC 200, as shown in greater detail in FIG. 6. It will be appreciated from FIG. 6 that the actual medical records advantageously can be stored in a buffer memory such as a redundant array of inexpensive drives (RAID) buffer memory or an optical memory such as an optical juke box. Preferably, the contents of the PBQs and PMBs are pointers, links or shortcuts to the actual EMRs containing the respective EMIs, which preferably are stored in RAID memory within or attached to CHC 200.

In contrast, PBQs allow diagnostic providers to compete with one another for the privilege of performing EMI readings. As discussed above, the patient/gatekeeper advantageously can choose to place the medical image on the "open market," i.e., so that the EMI will be addressed by the diagnostic physician community as a whole. It will also be noted that in this situation, the choice of diagnostic physician is relinquished in return for the opportunity to have the reading performed during what otherwise would be the diagnostic physician's average 30% downtime. Advantageously, even though the medical image is being placed in one of the PBQs, quality is maintained by virtue of the fact that all providers connecting to the CHC 200 preferably are Board Certified diagnosticians in their particular field.

The Patient Bid Queues (PBQs), in an exemplary case, are computer directories of Electronic Medical Records (EMRs) which are arranged according to the fee the patient chooses to bid for the reading of his/her EMI. A representative arrangement is illustrated in Table 2.

TABLE 2

| Statistics | $105 | $100 | $95 | $90 | $85 | $80 |
|---|---|---|---|---|---|---|
|  | — | — | — | — | — |  |
|  |  | — | — | — | — |  |
|  |  |  | — | — |  |  |
| # | 0 | 1 | 27 | 27 | 12 | 8 |
| Time | 0 | .5 | 25 | 48 | 120 | 1482 |

Additional details regarding each PBQ are listed immediately below the PBQ. For example, the line denoted # indicates the number of EMIs in each queue awaiting a reading. The line labeled Time indicates the estimated time in minutes to reach the top of the individual PBQ. Additional statistical information, such as that discussed above, advantageously can be provided to the patient/gatekeeper so as to permit informed selection of one of the PBQs.

It should again be mentioned that the above configuration of the PBQs is an exemplary arrangement; other arrangements are possible. For example, all medical images sent to the PBQs advantageously may be shown in a consolidated listing sorted on the bid price offered for the reading and the date-time the EMI is received by the CHC 200, as shown in greater detail in FIG. 6. As mentioned previously, the actual EMRs advantageously can be stored in a buffer memory such a redundant array of inexpensive drives (RAID) buffer memory or an optical memory such as an optical juke box; the contents of the PBQs and PMBs can be pointers, links or shortcuts to the actual EMRs containing the EMIs to be read, which advantageously can be stored in a RAID memory within or attached to CHC 200.

Still referring to step 600, the patient/gatekeeper displays the PBQs and information about each of the PBQs. In another exemplary case, the displayed information advantageously can be, but is not limited to, the following:

(1) The total number of patients in each of the PBQs (See "#" line in Table 2.);

(2) The average velocity through each of the PBQs (See the "Time" line depicted in Table 2.);

(3) The average velocity through each of the PBQs at a given time of the day; and (4) The estimated time when a reading would occur based on entry of the EMI at the current moment.

With this information at their disposal, the patient/gatekeeper advantageously can select an appropriate one of the PBQs reflective of the patient's needs and resources. When the patient's EMR containing a PBQ designation is transmitted to CHC 200, the operating system software of the CHC 200 automatically reads the appropriate field and assigns the patient's EMR to an appropriate location in the selected PBQ.

During step 602, a diagnostic image of the patient is generated at the imaging center 300. The diagnostic image is then digitized by scanner 320, in an exemplary case, and integrated with the electronic form stored in computer 310, which was previously provided by the gatekeeper's office, to produce the patient's EMR, i.e., the patient's Electronic Medical Record, which is then transmitted to the CHC 200 via the comm channel 210, also during step 602.

It should be mentioned that the exact order for performing steps 600 and 602 is not critical to the inventive method. For example, when the imaging facility is located in a hospital, the diagnostic image advantageously can be made first during step 602 and then the patient/gatekeeper can determine the best routing, i.e., to a PBQ or a PMB, for the patient's needs. However, when the imaging center is remote from the gatekeeper's office, the patient/gatekeeper advantageously can make a preliminary selection, since, as discussed in detail below, the patient's selection can be modified until the EMR is either previewed or selected by a diagnostic physician.

As mentioned above, the patient's EMR containing an associated EMI is transmitted from computer 310 to CHC 200 via comm channel 210, i.e., the EMR is sent from the imaging center 300 to the CHC 200. It should be noted that the only restriction on the method of transmission and, thus, on the comm channel itself, is that the transmission method used must guarantee that the patient's EMR received at CHC 200 is identical to the EMR residing at the imaging center 300. Those of ordinary skill in the digital communications art will appreciate that there are a myriad of methods for ensuring the transmission accuracy of the EMR, all of which are considered to be within the scope of the present invention. The method employed in implementing comm channel 210 is solely determined by the imaging center's abilities and the patient's needs and financial resources. It should be clearly understood that the particular implementation of the comm channels has no bearing on the present invention as long as it maintains the digital integrity of the EMR.

Once the EMR with it's included EMI is received by CHC 200, the computer's operating system stores the EMR in the EMR Storage area and searches the stored EMR for the particular field which contains the information specifying the location where the patient's EMR is to be entered, i.e., either into one of the PBQs or one of the PMBs. The operating software of the CHC 200 then places the Document Control Number corresponding to the patient's EMR in the appropriate Patient Bid Queue (PBQ) or Provider Mail Box (PMB). The operating program then advances to step 604.

The progress of the EMI through the selected PBQ or PMB advantageously can be monitored during step 604. The computer 510 at the gatekeeper's office 500, and possibly, the computer 310 at the imaging center 320, preferably includes software which allows the patient or the patient/gatekeeper to monitor the progress of the patient's EMI through the chosen location, i.e., chosen PBQ or PMB. See, for example, the comm channel 240 in FIG. 3. By highlighting or selecting the DCN for his/her EMR, the patient will be able to determine the relative velocity of his/her EMR through the selected PBQ or PMB. It will be appreciated that a negative velocity indicates that the patient's EMR is being driven further down the overall prioritized list of EMRs awaiting readings by other patients who are bidding more for the downtime of the pool of diagnostic physicians. As noted in FIG. 3, this monitoring advantageously can be performed, in an exemplary case, over normal phone lines and a pair of modems 232, 242.

During step 604, the patient reviews the progress of his/her own EMR to determine subjectively whether the velocity through the PBQs or selected PMB is acceptable. When the patient/gatekeeper decides that progress is unacceptable to the patient, the patient/gatekeeper advantageously can remotely request that the priority the patient attaches to his/her EMI be increased, i.e., the patient/gatekeeper can change the bid price. For example, if the patient notes that his/her EMR currently has a negative velocity, the patient/gatekeeper could simply increase the bid price by changing the information on the selection field of the patient's EMF and transmitting the change to CHC 200 via comm channel 240 during step 608. When the patient's corresponding EMR on CHC 200 is updated with the new bid price, the DCN for the patient's EMR would move from its current position to the bottom of the newly selected one of the PBQs. By changing to a "higher" PBQ, the patient will shorten the time period until his/her EMR will be read, i.e., the estimated time of reading the associated EMI will be moved up. This process allows for the continuous negotiation of the bid price, i.e., it creates a free market environment.

During steps 600, 602, 604, and 606, the patient/gatekeeper retained control of the patient's EMI contained in a respective EMR; once the diagnostic physician starts the evaluation of the patient's EMI at step 608, the patient/gatekeeper will no longer be able to effect changes to the patient's bid price, at least in the preferred embodiment according to the present invention being discussed.

As a diagnostic physician goes through his/her day, there are moments when the diagnostic physician suddenly finds himself with 15–20 minutes of downtime, i.e., with no readings to perform. During this downtime, the diagnostic physician advantageously can access the RAMIX system, represented by CHC 200 in FIG. 3, and examine the PBQs, starting with the highest-ranked active PBQ. There, the diagnostic physician sees the pool of waiting patients and the amount they are willing to pay the diagnostic physician for diagnostic services. In the event that the diagnostic physician desires to perform a reading of an EMI, the diagnostic physician can request that the EMR carrying the highest bid price be downloaded to him. It should be noted that as far as the service provider is concerned, this is equivalent to having a "just in time" image to read.

As an example, in a large community such as New York City there are several hundred radiologists. At any given moment there will always be a significant number who have no EMIs to read. The inventive method and system therefor provide the patient with a way of negotiating with all idle diagnostic physicians as a group to do the patient's reading. Advantageously, this means that a central administration, i.e., a middle man, is completely unnecessary.

Each diagnostic reading site, e.g., hospital or diagnostic physician's office 400, includes a computer 410 with operating software capable of connecting the computer 410 to the CHC 200 via both comm channels 220 and 230. When one of the diagnostic physician's local work load permits, that diagnostic physician connects to CHC 200 to check both his/her personal PMB and the PBQs during step 608. If the diagnostic physician chooses to examine the PBQs, the information displayed in area 414 of the screen of computer 410 preferably corresponds to the active PBQ with the highest bid price. Preferably, the DCNs of the patient's EMRs for the highest active PBQ are listed in time of receipt order. If the diagnostic physician is willing to perform a reading for the bid price, the diagnostic physician requests that the patient's EMI and corresponding EMR be downloaded to him. Preferably, this subroutine includes steps for screening the EMIs, during steps 608 and 610, as well as downloading the EMR containing the selected EMI during step 612, as discussed in greater detail below. If the diagnostic physician chooses not to do a reading for an image in this area, the diagnostic physician can either transfer to another array area, or to his/her PMB, or sign off the RAMIX system. These additional steps (not shown) can be implemented when the response at step 610 is negative.

During step 608, the diagnostic physician receives a list of DCNs corresponding to the patient EMIs available for reading. The diagnostic physician selects the first DCN in the list. This selection results in several simultaneous actions in CHC 200. First, all of the other diagnostic physicians reviewing the same PBQ are locked out of the EMR having the selected EMI. Second, the CHC 200 transmits the EMR including patient information from the EMF, which preferably is displayed in area 412 on the screen of computer 410, and a preview image corresponding to either the sole or first digitized diagnostic image in the patient's EMI. It will be appreciated that the size of the actual digitized diagnostic image, which may be in excess of 50 Mbits, is too large for downloading. However, a decimated version of that image advantageously can be downloaded over very low speed comm channel 230 in a few seconds. While a digital image of 50–100 Kbits is not sufficient to allow the diagnostic physician to render a diagnosis, that digital image includes sufficient detail to allow the diagnostic physician to determine, during step 610, whether he/she desires to read the particular EMI. When the diagnostic physician does not wish to read the currently previewed EMI, the diagnostic physician rejects the EMI and the DCN is deselected; thus, the other diagnostic physicians are no longer locked out of the rejected EMI.

It will be appreciated that, alternatively, the diagnostic physician merely receives a list of arrays of PBQs, each array having patient EMIs available for reading during step 608. He/she is also told what the highest bid price is in each array. When he/she subsequently selects one of the arrays, it results in several simultaneous actions in CHC 200. First, the CHC 200 automatically picks the highest current bid EMI in the selected array and locks out all other diagnostic physicians from that EMI. Second, the CHC 200 transmits patient information, which preferably is displayed in area 412 on the screen of computer 410, and a preview image corresponding to either the sole or first digitized diagnostic image in the patient's EMI. As previously mentioned, the size of the actual digitized diagnostic image is too large for downloading; a decimated version of that image advantageously can be downloaded over low speed comm channel 230 in a few seconds, so that the diagnostic physician can determine, during step 610, whether he desires to read the particular EMI. When the diagnostic physician does not wish to read the currently previewed EMI, the diagnostic physician rejects the EMI and it is deselected; thus, the other diagnostic physicians are no longer locked out of the EMI.

Thus, if for any reason the physician decides not to read the patient's EMI, the diagnostic physician can reject the EMR containing the EMI, which EMR will then be placed back at the top of the selected PBQ. It will be appreciated that the diagnostic physician is under no obligation to read an EMI. On the other hand, the diagnostic physician has an obligation, once he/she has started to preview the EMI, to either read the EMI or refuse it quickly. In short, the diagnostic physician must select the DCN of a corresponding EMR, preview the EMI contained therein, and decide whether he/she will read or refuse the image. This measure is designed to eliminate the possibility of EMI stockpiling by radiologists, e.g., radiologists who may otherwise come in the morning and start downloading EMIs but won't read the EMIs until much later in the day.

When the diagnostic physician desires to read the previewed EMI, the diagnostic physician requests that the EMR with its associated EMI be downloaded from CHC 200 to computer 410 via high speed comm channel 220, during step 612. Unlike the comm channel 210 between computer 310 and CHC 200, where the method and speed of transmission is irrelevant, the speed of transmission using comm channel 220 between the CHC 200 and the diagnostic physician's office 400 is crucial. In order to efficiently employ the downtime of the diagnostic physician pool, which downtime tends to come at unpredictable times and be of short duration, the EMIs must not only be ready when the diagnostic physician is ready but must be capable of being downloaded rapidly. For example, a typical radiology image could be as large as 50 MB. Therefore, to take advantage of the typical 15 minute downtime, the patient's EMI should be completely downloaded in one or two minutes. For that reason, high bandwidth links, e.g., 1 Mbit/sec or higher, are particularly advantageous. Thus, as discussed above, the high speed comm channel 220 advantageously could be provided by a T1 line, a satellite comm system, cable modem lines equipped for bulk data transmission, etc. It will be appreciated that transmission of the complete EMR advantageously can be downloaded in substantially the same time, since the difference between the EMI and the complete EMR is the EMF.

It should also be mentioned that given sufficient bandwidth in comm channel 220, the process of downloading the patient's EMR containing the image to be read could also include additional image processing operations beyond the basic image transfer. For example, during step 608, the diagnostic physician determines that the x-ray is that for a hand; the diagnostic physician also determines that he/she should pay particular attention to the index finger of that hand. By selecting a particular area of the x-ray during preview step 608, the diagnostic physician can download both the original EMI and a blown up (enlarged) image corresponding to the selected area of the x-ray. In other exemplary cases, the diagnostic physician can order edge enhancement of an x-ray, image subtraction to remove skeletal features when the soft tissue is of interest, or vice versa, and computer-aided screening for tumors and precancerous lesions. Thus, the CHC 200 first downloads the EMI itself and then downloads the requested value-added image(s). It will be appreciated that the RAMIX system advantageously can provide diagnostic programs which otherwise would be too expensive for the average radiology group to afford, e.g., those located in rural areas.

During step 614, the diagnostic physician reads the patient's EMI, i.e., the patient's EMI appears on the screen of the computer 410 and the diagnostic physician performs his/her diagnosis and prepares his/her written diagnosis report. When the written diagnosis report for the reading has been completed, the diagnostic physician transmits his/her diagnosis during step 616 via 618, the CHC 200 transmits the written diagnosis report to the computer 510 in the patient/gatekeeper's office 500 via comm channel 240, in an exemplary case. It will be appreciated that the report may be routed to the patient/gatekeeper by any conventional method selected by the patient/gatekeeper, although the report may advantageously be transmitted to CHC 200 so as to prevent the RAMIX system from falsely determining that the EMI has not been read in a timely fashion, as discussed in detail below.

It should be mentioned that area 416 of the screen of the computer 410 advantageously displays a form for recording the diagnostic physician's reading and that the digitized diagnostic image forming the EMI advantageously can be displayed on the area 418 of the screen of computer 410. The screen of computer 410 is preferably a high resolution graphic display monitor and not a conventional SVGA computer monitor. Advantageously, the diagnostic physician reads the digitized diagnostic image and writes his/her diagnosis directly into the form provided in computer screen area 416. The diagnostic physician advantageously can employ voice recognition software with a specialized medical dictionary module to improve his/her efficiency still further.

It should also be mentioned that in the exemplary case being discussed all EMIs have a predetermined time limit within which the EMI must be read once it has been uploaded to computer 410, as discussed above; if a diagnosis has not been uploaded to the CHC 200 from the computer 410 within a predetermined period of time, the patient's EMR is placed back in the PBQ from whence it came and the diagnostic physician who failed to respond in a timely manner is not allowed to file a diagnosis report. Moreover, the operating software of the CHC 200 advantageously can contain features to lock out a diagnostic physician who repeatedly fails to submit a timely diagnosis within the allotted predetermined period of time.

It will be appreciated that many alternative methods for operating the RAMI system advantageously can be employed within the scope of the present invention. For example, it would be possible to operate the system on a flat fee basis. In this alternative embodiment, the patient transmits his/her EMR containing the EMI to the CHC 200 via comm channel 210, as discussed above. With this configuration, instead of a plurality of PBQs with different bid prices, there is only one PBQ. DCNs for corresponding EMRs are placed in the single PBQ, with the DCNs arranged in time of receipt order. When a diagnostic provider has downtime and wishes to perform a reading, the diagnostic physician connects to the RAMX system and downloads an EMR containing the selected EMI.

It will be noted that this alternative embodiment i.e., non-bid patient queues, provides only reasonable time delivery of EMIs but still achieves greater efficiency and improved health care. It should be mentioned that since no direct bidding is permitted, patients have no mechanism to indicate the subjective priority of their EMIs to the diagnostic physician. In this alternative embodiment of the present invention, patients are charged a flat rate while providers are given a flat fee. All other technical aspects of the RAMIX system are the same as illustrated in FIG. 3.

Advantageously, the flat rate method could be employed by an institution that wishes to lock in a predetermined price and for diagnostic providers who wish to lock in a predetermined fee. For example, VA Hospitals could employ this method to reduce their overall operating costs for diagnostic services.

It should also be mentioned that the alternative preferred embodiment could be operated in parallel with the system according to the preferred embodiment. This would pose no technical problems as access to the flat fee portion of the overall system could easily be restricted to particular patients and predetermined diagnostic providers. In the exemplary case under discussion, the RAMIX system is still a self-organizing distribution system providing "just in time images."

Another interesting alternative method for operating the RAMIX system according to the present invention is the so-called open market direct bid method of operation. In an exemplary case, the patient transmits his/her EMR to CHC 200 via comm channel 210 as a work order the patient would like to receive bids on. The diagnostic physicians currently experiencing downtime would then bid against one another for the privilege of performing the reading. Advantageously, a time limit is established, e.g., one hour, and during that time diagnostic physicians would bid on performing the reading. At the end of the predetermined time period, the diagnostic physician with the lowest bid would be awarded the reading. It should be mentioned that with this particular method of operating the RAMIX system, the diagnostic physicians bidding for a particular reading would be bidding for an EMI which could be read during the next down period that occurs after the bidding closes. It should also be mentioned that the bids need not be restricted to monetary amounts. Patients are free to establish other criteria for the successful bidder such as: how fast the reading must be done; the type of subspecialty the diagnostic physician must have, etc. All of these factors and more advantageously could go into evaluating the bids and determining the successful bidder. It will noted that the RAMIX system performs the evaluation according to the criteria established by the patient/gatekeeper.

In summary, the RAMIX system according to the present invention changes the dynamics of the interaction between patients and the diagnostic providers by acting as a buffer storing EMIs while a contract for diagnostic services is formed between a patient and a diagnostic physician. Moreover, the RAMI system according to the present invention provides "managed care", i.e., it is managed by the patient and the provider, in contrast with most so-called "managed care organizations", which are really organizations chartered to "limit care." Since the RAMI system provides patients with an avenue for bidding on the average 30% downtime experienced by most diagnostic physicians, the RAMIX system and the corresponding method of operation according to the present invention provide a mechanism for reducing the average cost of diagnostic services. Thus, the rates for such services should be considerably lower. Moreover, the improved efficiency made possible by employing the RAMIX system according to the present invention could result in the elimination of 10% to 20% of the currently practicing diagnostic providers, e.g., physicians who are not board certified in their avowed specialty.

Advantageously, the RAMIX system and the corresponding operating system according to the present invention are designed to automate the overall process of diagnostic delivery and reporting. It will be appreciated that there are readings that are now considered undesirable because of the radiologists' perception that they can't "make any money" on these readings. But it isn't the type of EMI that is the problem, it's the inefficient fashion in which the EMR and its included EMI is usually handled. If the distribution process could be made more efficient, this type of EMI would be more desirable, or at least less undesirable. It will also be appreciated that the RAMIX system could also be coordinated with electronic claims processing systems and methods such as those disclosed in copending, commonly owned application Serial Nos. 08/823,979, 08/824,010, and 08/823,978, which applications are incorporated herein by reference for all purposes.

Advantageously, the RAMIX system and corresponding operating method according to the present invention provide a mechanism for obtaining what amounts to "service on demand" at a discount price. It will be appreciated that, at present, there are no differences between readings done on an emergency basis and those performed on a routine basis. The RAMI system provides a mechanism for doing emergency readings, with only a small premium being paid for the expedited service. That is, the patient/gatekeeper examines the Patient Bid Queues, finds the highest bid price, and then bids a little higher.

Beneficially, the RAMIX system and corresponding operating method could be used, because of the potentially fast turn around time, to bring readings back into the radiology world that are currently being done by non-diagnostic physicians, e.g. orthopedists and chiropractors. This also permits malpractice insurance companies to lower premiums for providers who use the service. Having a diagnostic physician do the reading instead of a chiropractor would improve the general health care of the patient while at the same time lowering the malpractice risk exposure of the chiropractor. It will be appreciated that in the New York City area alone, chiropractors generate approximately 1,000 images per day.

With respect to improvements in overall health care, it will be appreciated that the method of operating the RAMIX system could accommodate all Managed Care Organizations that demand that their patients put their EMIs on this system, assuming that the Managed Care operator could receive a lower cost for diagnostic services. Additionally, the Managed Care operator might demand that all affiliated providers be connected to the RAMI system. Moreover, the RAMIX system has the potential to expand and improve the quality of radiological/image read/diagnostic services which are available in rural and other presently "under serviced areas."

It should also be mentioned that the method of operation of the RAMIX system could be modified to accommodate second opinions. For example, the patient/gatekeeper could desire a second opinion. When completing the EMF of the EMR, the patient/gatekeeper could include a code in one of the fields indicative of this preference. When the EMR and its associated EMI is uploaded to CHC 200, the EMR goes to the storage area and two different DCNs go into the selected PBQ, with the first and second DCNs being time separated from one another by a predetermined time interval or a time interval based on velocity through the selected PBQ. When both of the DCNs are selected, the EMI is downloaded twice and two independent readings are performed. When the CHC 200 receives both readings from the diagnostic physicians, the CHC 200 forwards them both to the patient/gatekeeper.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A buffer memory for storing a plurality of digital information blocks generated by a plurality of respective first users in an order established by said first users,
    wherein each of said digital information blocks is receivable by at least one of a plurality of second users,
    wherein each of said digital information blocks includes a bid price offered by said first users to said second users to thereby indicate the priority one of said users attaches to an associated one of said digital information blocks, and
    wherein one of said second users elects to receive one of said digital information blocks responsive to said bid price of a respective digital information block.

2. The buffer memory as recited in claim 1, wherein said digital information blocks are electronic medical images.

3. The buffer memory as recited in claim 1, wherein any one of said first users can freely change said bid price of the associated one of said digital information blocks.

4. A storage medium for storing computer readable instructions for permitting a computer to store a plurality of electronic medical images corresponding to respective first users, to arrange said electronic medical images in a bid price order established by all of said first users, and to download one of said electronic medical images to a requesting one of a plurality of second users based on the bid price order established by said first users.

5. The storage medium as recited in claim 4, wherein said second users are diagnostic physicians.

6. The storage medium as recited in claim 4, wherein said storage medium is a hard drive disposed in a computer.

7. A storage medium for storing computer readable instructions for permitting a computer to store a plurality of first electronic medical images corresponding to respective first users, to store a plurality of second electronic medical images corresponding to respective second users, to arrange said first electronic medical images in a first order established by all of said first users, to arrange said second electronic medical images in a second order established by all of said second users, to download one of said first electronic medical images to any requesting one of a plurality of third users based on the order established by said first users, and to download one of said second electronic medical images to one of said third users selected by one of said second users.

8. The storage medium as recited in claim 7, wherein said storage medium stores computer readable instructions for instructing the computer to store said first electronic medical images in a plurality of queues, each of said queues storing respective ones of said first electronic medical images having a respective predetermined indicia of the priority assigned by each of said first users.

9. The storage medium as recited in claim 7, wherein said storage medium stores computer readable instructions for instructing the computer to permit said first users to become said second users, and vice versa, until a selected one of said first and said second electronic medical images is downloaded by one of said third users.

10. A combination comprising:
    a first record medium for storing computer readable instructions for permitting a first computer to store a plurality of first electronic medical images corresponding to respective first users, to store a plurality of second electronic medical images corresponding to respective second users, to arrange said first electronic medical images in a first order established by all of said first users, to arrange said second electronic medical images in a second order established by all of said second users, to download one of said first electronic medical images to any requesting one of a plurality of third users based on the order established by said first users, and to download one of said second electronic medical images to one of said third users selected by one of said second users;
    a second record medium for storing computer readable instruction for permitting a second computer to generate said first and said second electronic medical images;
    a third record medium for storing machine readable instructions for permitting a third computer to monitor a relative position of a selected one of said first and second electronic medical images and for instructing said first computer to move said selected one of said first and second electronic medical images to a new position in one of the orders established by said first and said second users; and a fourth record medium for storing computer readable instructions for permitting a fourth computer to download said requested one of said first and said second electronic medical images.

11. The combination as recited in claim 10, wherein said first, said second, said third and said fourth storage media comprise respective hard disks.

12. The combination as recited in claim 10, wherein said first and said second electronic medical images are digitized x-rays.

13. The combination as recited in claim 10, wherein said first and said second electronic medical images each include an indicia of the priority a respective one of said first and said second users attaches to processing of respective first and second electronic medical images by said third users.

14. The combination as recited in claim 13, wherein said machine readable instructions for instructing said first computer to move said selected one of said first and second electronic medical images to a new position in one of the orders established by said first and second users comprises changing said indicia in said first and said second electronic medical images.

15. The combination as recited in claim 10, wherein said instructions in said fourth storage medium permit said selected electronic medical image to be displayed on said fourth computer.

16. A system for transmitting, storing, retransmitting and receiving a plurality of electronic medical images, each containing an indicia of the priority attached to one of the electronic medical images by a respective patient, said system comprising:

a first computer system including:
 a first memory storing a first software module containing first operating instructions readable by said first computer system; and
 a scanning device for generating the electronic medical images;

a first communications channel receiving said electronic medical images from said first computer system;

a second computer system receiving the electronic medical images from said first communications channel, said second computer system including:
 a second memory storing a second software module containing second operating instructions readable by said second computer system;
 an electronic medical image storage memory for storing links to the electronic medical images in a predetermined order based on the indicia in the respective electronic medical images; and a second communications channel for receiving a selected one of the electronic medical images from said second memory;

a third computer system for selecting said selected one of the electronic medical images and for receiving said selected one of said electronic medical images, said third computer comprising:
 a third memory storing a third software module containing third operation instructions readable by said third computer; and
 a first display for displaying said selected one of the electronic medical images;

a third communications channel; and a fourth computer system operatively coupled to said second computer system by said third communications channel, said fourth computer system comprising:

a second display for monitoring all of said electronic medical images; and an input device for changing one of the indicia in a respective one of the electronic medical images;

wherein said second computer system, under control of said second operating instructions, reorders all of said links to the stored electronic medical images responsive to the change of any one of the indicia of the electronic medical images.

17. The system as recited in claim 16, wherein said second communications channel comprises:

a low speed communications channel for instructing said second computer system to download the selected one of the electronic medical images to said third computer system; and a high speed communications channel for downloading said selected one of the electronic medical images from said second computer system to said third computer system.

18. The system as recited in claim 16, wherein said third computer system comprises a plurality of third computers, and wherein said electronic medical image storage memory comprises a first electronic medical image storage memory accessible by all of said third computers and a second electronic medical image storage memory having a plurality of partitions, each of said partitions being accessible by only a selected one of said third computers.

19. The system as recited in claim 18, wherein a one-to-one correspondence between said partitions and a subset of said third computers is established by respective passwords.

20. A method for operating a computer system including a buffer memory storing a plurality of electronic medical images awaiting diagnosis by a diagnostic physician, each of the electronic medical images having an associated priority indicia assigned by a respective user, said method comprising steps for:

storing a patient's electronic medical image among the plurality of electronic medical images;

monitoring a rate of change of position of the patient's electronic medical image relative to the plurality of electronic medical images to thereby determine velocity through the buffer memory to the diagnostic physician; and when said velocity is unacceptable to the patient, changing the priority indicia in the patient's electronic medical image so as to instruct the computer system to reorder the plurality of electronic medical images based on the priority indicia and thereby adjust the velocity of the patient's electronic medical image through the buffer memory.

21. The method as recited in claim 20, wherein the priority indicia correspond to a price bid by the patient to the diagnostic physician for performing the diagnosis.

22. The method as recited in claim 20, further comprising the step for downloading the one of the electronic medical images having the highest priority to the diagnostic physician.

23. A method for operating a computer system including a first buffer memory storing a plurality of first electronic medical images awaiting diagnosis by one of a plurality of diagnostic physicians and a second buffer memory storing a plurality of second electronic medical images awaiting diagnosis by a selected diagnostic physician, each of the electronic medical images having an associated priority indicia assigned by a respective user, said method comprising steps for:

storing a patient's electronic medical image among a selected one of the first and second electronic medical images;

monitoring a rate of change of position of the patient's electronic medical image relative to the selected one of the first and second electronic medical images to thereby determine velocity through one of the first and second buffer memories; and when said velocity is unacceptable to the patient, changing the priority indicia in the patient's electronic medical image so as to instruct the computer system to reorder the selected one of the first and second electronic medical images based on the priority indicia and thereby adjust the velocity of the patient's electronic medical image through the selected one of the first and second buffer memories.

24. The method as recited in claim 23, wherein changing the priority indicia permits transfer of the patient's electronic medical image from the first buffer memory to the second buffer memory, and vice versa.

25. A remote access medical image exchange system, comprising:

a first facility for converting a plurality of physical medical images for respective patients into corresponding digital medical images and for storing the digital medical images in a remotely accessible data storage device, to thereby provide a remotely accessible electronic digital medical image database comprised of the stored digital medical images;

a plurality of second facilities remote from the first facility, but in electronic communication therewith, for providing a pool of participating diagnostic service providers with access to the electronic digital medical image database; and, wherein the system is configured in such a manner as to enable any one or more of the diagnostic service providers to select one or more of the digital medical images from the database for reading, in accordance with selection criteria established by one of the diagnostic service providers and the patients.

26. The system as set forth in claim 25, wherein the selection criteria include estimated time of reading and price.

27. The system as set forth in claim 25, wherein the selection criteria include diagnostic service provider capability and availability.

28. The system as set forth in claim 26, wherein the selection criteria further include diagnostic service provider capability and availability.

29. The system as set forth in claim 25, wherein the system is configured in such a manner as to enable any one or more of the diagnostic service providers to select one or more of the digital medical images from the database for reading at any time which they choose.

30. The system as set forth in claim 29, wherein the time of their choosing includes diagnostic service provider downtime.

31. The system as set forth in claim 25, further comprising means for facilitating interactive bidding by the patients and diagnostic service providers regarding the fees to be charged by the participating diagnostic service providers for the reading of one or more of the digital medical images from the database, whereby the system functions as an open electronic marketplace for the reading of digital medical images.

32. The system as set forth in claim 25, further comprising means for facilitating competitive bidding by the diagnostic service providers for the reading of at least some of the digital medical images stored in the database.

33. The system as set forth in claim 25, further comprising means for providing the patients access to biographical information concerning the diagnostic service providers.

34. The system as set forth in claim 33, further comprising means for providing the patients access to pricing information for the reading of the digital medical images.

35. The system as set forth in claim 34, wherein the pricing information includes a schedule of fees for the reading of different types of the digital medical images.

36. The system as set forth in claim 34, wherein the pricing information includes a listing of the fees charged by different ones of the diagnostic service providers.

37. The system as set forth in claim 34, wherein the pricing information includes:

a schedule of fees for the reading of different types of the digital medical images; and a listing of the fees charged by different ones of the diagnostic service providers.

38. A method for facilitating remote reading of medical images, including the steps of:

converting a plurality of physical medical images for respective patients into corresponding digital medical images;

storing the digital medical images in a remotely accessible data storage device, to thereby provide a remotely accessible electronic digital medical image database comprised of the stored digital medical images;

providing a pool of participating diagnostic service providers with access to the electronic digital medical image database; and wherein any one or more of the diagnostic service providers can select one or more of the digital medical images from the database for reading, in accordance with selection criteria established by the diagnostic service providers and the patients.

39. The method as set forth in claim 38, wherein any one or more of the diagnostic service providers can select one or more of the digital medical images from the database for reading any time which they choose.

40. The method as set forth in claim 38, wherein any one or more of the diagnostic service providers selects one or more of the digital medical images from the database during their normal downtime.

41. The method as set forth in claim 38, further including the step of the participating diagnostic service providers competitively bidding for the right to read one or more of the digital medical images from the database.

42. The method as set forth in claim 38, further including the step of the participating diagnostic service providers and the patients engaging in an interactive bidding process regarding the fees to be charged by the participating diagnostic service providers for the reading of one or more of the digital medical images from the database.

43. The method as set forth in claim 38, further including the step of providing the patients access to biographical information concerning the qualifications of the participating diagnostic service providers.

44. The method as set forth in claim 38, further including the step of providing the patients access to pricing information for the reading of the digital medical images.

45. The method as set forth in claim 44, wherein the pricing information includes a schedule of fees for the reading of different types of the digital medical images.

46. The method as set forth in claim 44, wherein the pricing information includes a listing of the fees charged by different ones of the diagnostic service providers.

47. The method as set forth in claim 44, wherein the pricing information includes:

a schedule of fees for the reading of different types of the digital medical images ; and a listing of the fees charged by different ones of the participating diagnostic service providers.

48. A method for operating a computer system including a buffer memory storing a plurality of electronic medical by diagnosis by a diagnostic physician, each of the electronic medical images having an associated priority indicia assigned by a respective user, said method comprising steps for:

monitoring a rate of change of position of the patient's electronic medical image relative to the plurality of electronic medical images;

estimating a velocity through the buffer memory to the diagnostic physician; and when said velocity is unacceptable to the patient, changing the priority indicia in the patient's electronic medical image so as to instruct the computer system to reorder the plurality of electronic medical images based on the priority indicia and thereby increase the velocity of the patient's electronic medical image.

49. The method as recited in claim 48, wherein the priority indicia correspond to a price bid by the patient to the diagnostic physician for performing the diagnosis.

50. The method as recited in claim 48, further comprising the step for downloading the one of the electronic medical images having the highest priority to the diagnostic physician.

* * * * *